US009168051B2

(12) United States Patent
Weisenburgh, II et al.

(10) Patent No.: US 9,168,051 B2
(45) Date of Patent: Oct. 27, 2015

(54) LAPAROSCOPIC DEVICE WITH THREE JAWS

(75) Inventors: William B. Weisenburgh, II, Maineville, OH (US); Gregory J. Bakos, Mason, OH (US); Omar J. Vakharia, Cincinnati, OH (US); David Stefanchik, Morrow, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 980 days.

(21) Appl. No.: 13/250,272

(22) Filed: Sep. 30, 2011

(65) Prior Publication Data
US 2013/0085494 A1    Apr. 4, 2013

(51) Int. Cl.
| A61B 10/00 | (2006.01) |
| A61B 17/29 | (2006.01) |
| A61B 18/08 | (2006.01) |
| A61B 18/14 | (2006.01) |
| A61B 17/04 | (2006.01) |
| A61B 17/062 | (2006.01) |

(52) U.S. Cl.
CPC ............. *A61B 17/29* (2013.01); *A61B 17/0469* (2013.01); *A61B 17/062* (2013.01); *A61B 18/085* (2013.01); *A61B 18/1445* (2013.01); *A61B 2017/2926* (2013.01); *A61B 2017/2938* (2013.01); *A61B 2017/2945* (2013.01)

(58) Field of Classification Search
CPC ........... A61B 18/1442; A61B 18/1445; A61B 18/1492; A61B 18/085; A61B 17/0469; A61B 17/062; A61B 17/29
See application file for complete search history.

(56) References Cited

U.S. PATENT DOCUMENTS

| 5,441,494 A * | 8/1995 | Ortiz ................................. 606/1 |
| 5,776,075 A * | 7/1998 | Palmer ........................... 600/564 |
| 2008/0234725 A1* | 9/2008 | Griffiths et al. ................ 606/208 |
| 2010/0249769 A1* | 9/2010 | Nau et al. .......................... 606/33 |
| 2012/0095298 A1* | 4/2012 | Stefanchik et al. ............ 600/219 |

* cited by examiner

*Primary Examiner* — Scott Getzow
(74) *Attorney, Agent, or Firm* — Mintz Levin Cohn Ferris Glovsky and Popeo, P.C.

(57) ABSTRACT

Methods and devices are provided utilizing an end effector having three jaws movably coupled thereto for grasping and/or dissecting tissue. In one embodiment, each of the three jaws are movable between an open position in which the distal ends of the three jaws are spaced apart from one another, and a closed position in which the distal ends directly contact one another. The jaws can define an opening therebetween when the jaws are in the closed position.

18 Claims, 14 Drawing Sheets

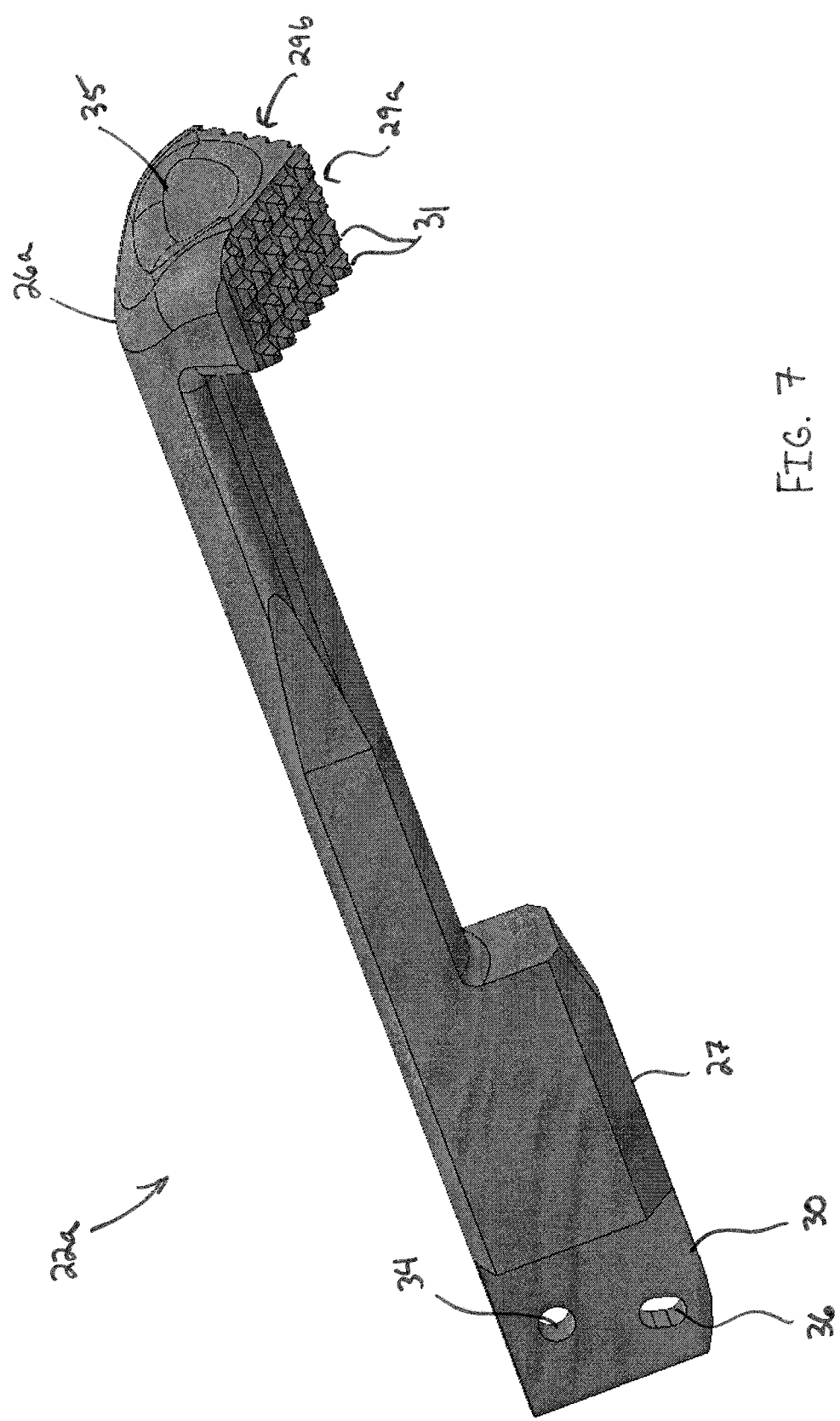

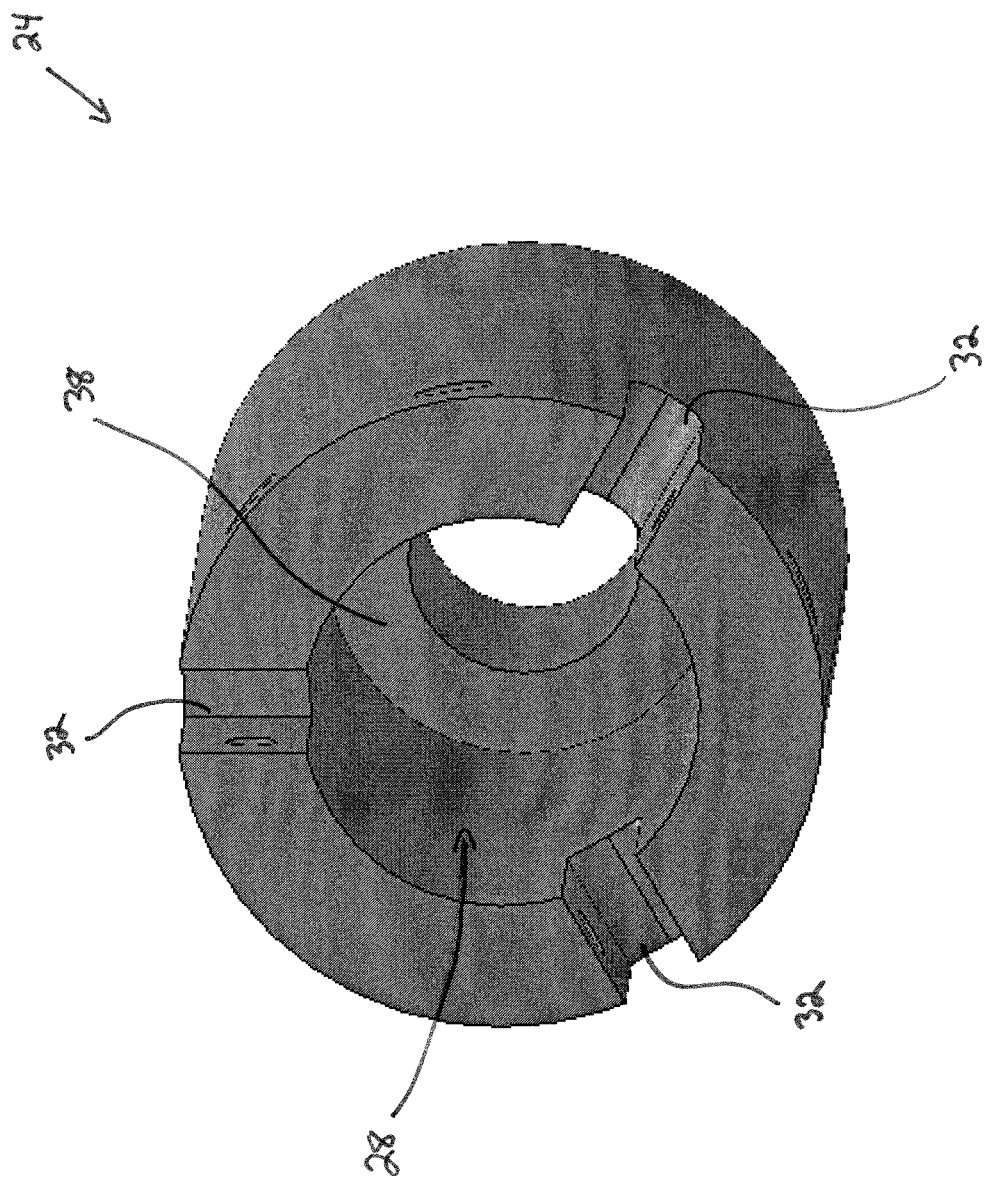

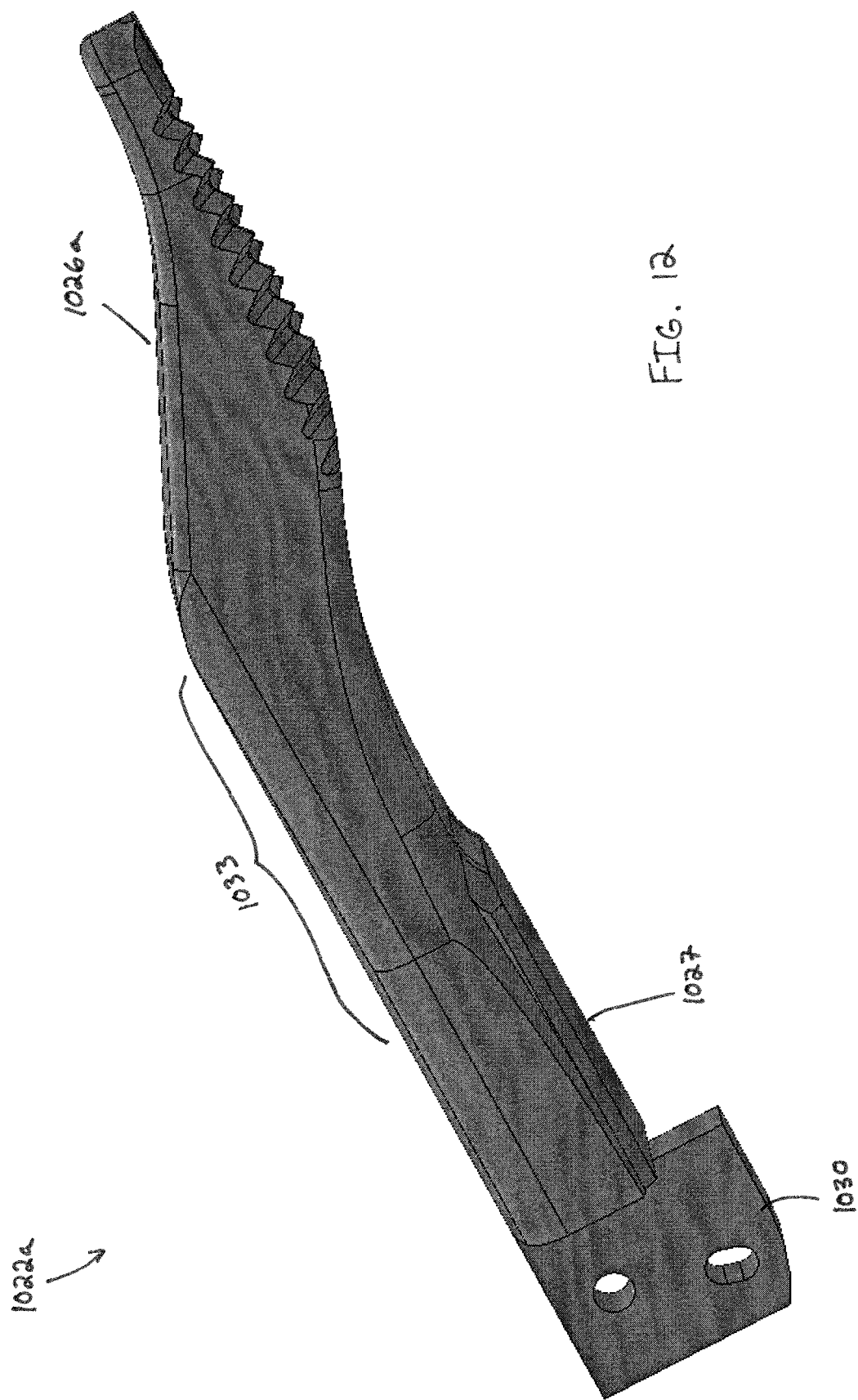

LAPAROSCOPIC DEVICE WITH THREE JAWS

FIELD OF THE INVENTION

The present invention relates to laparoscopic grasping and/or dissecting devices, and methods for grasping and/or dissecting tissue.

BACKGROUND OF THE INVENTION

Minimally invasive surgical (MIS) instruments are often preferred over traditional open surgical devices due to the reduced post-operative recovery time and minimal scarring associated with minimally invasive procedures. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. Endoscopic surgery is another type of MIS procedure in which elongate flexible shafts are introduced into the body through a natural orifice.

Due to the benefits associated with minimally invasive surgeries, significant efforts have gone into developing a range of endoscopic and laparoscopic surgical instruments that are suitable for precise placement of a distal end effector at a desired surgical site. These distal end effectors engage the tissue in a number of ways to achieve a diagnostic or therapeutic effect (e.g., grasper, cutter, staplers, clip applier, access device, drug/gene therapy delivery device, and energy device using ultrasound, RF, laser, etc.).

For example, end effectors for grasping tissue have been developed which secure tissue between two jaws. Though two-jawed graspers can be effective to engage tissue therebetween, graspers must exert significant compressive forces on the target tissue in order to insure a firm grasp. Due to the constraints of operating in confined spaces, however, graspers must often utilize relatively small tissue-engaging surfaces which decrease the tissue area to which the force is applied, thereby leading to increased risk of unintentional tissue damage. Merely increasing the size of the grasper is impractical, however, as such efforts are limited by the size of the access port and the surgeon's need to visualize the surgical site and/or deliver multiple end effectors thereto. Further, the limited range of motion of the two-jawed graspers can make it difficult to occlude a puncture site, for example, as the two jaws must be precisely aligned with target tissue site to ensure capture. Similarly, two-jawed end effectors for dissecting (e.g., separating or spreading) tissue can lead to unintentional tissue damage tissue due to the pressure placed on the tissue by the two jaws, while possibly limiting the access due to the end effector's lack of freedom of movement. For example, conventional two-jawed dissectors typically generate an elongate access slot in the dissected tissue.

Accordingly, there remains a need for improved end effectors and methods of operating the same, and in particular to methods and devices for grasping or dissecting tissue.

SUMMARY OF THE INVENTION

The present invention generally provides surgical methods and devices utilizing an end effector having three jaws movably coupled thereto for grasping and/or dissecting tissue. In one embodiment, a surgical device is provided having an end effector with first, second, and third atraumatic jaws movably coupled thereto. Each jaw has a proximal end and a distal end and is movable between an open position in which the distal ends of the three jaws are spaced apart from one another and a closed position in which the distal ends directly contact one another. In one embodiment, the device can include a handle, an elongate shaft extending distally from the handle, and an actuation mechanism extending between the handle and the end effector for moving the jaws between the open and closed positions. The end effector can, for example, be rotatable relative to the handle.

The end effector and its jaws can have a variety of configurations. For example, in one embodiment, the jaws can be positioned symmetrically about a longitudinal axis of the end effector. In one embodiment, at least one of the first, second, and third jaws can be independently movable relative to the other jaws. For example, one of the jaws can be independently movable between the open position and the closed position relative to the other jaws. In another embodiment, at least one of the jaws can be longitudinally retractable relative to the other jaws.

The distal portion of the jaws can be configured to engage tissue therebetween. Each jaw can have a substantially triangular-shaped distal-most tip. In one embodiment, each jaw can have first and second substantially planar tissue-grasping surfaces. The first and second surfaces can extend, for example, at an obtuse angle relative to one another.

In one embodiment, at least one of the jaws can be configured to delivery energy to the tissue. By way of example, at least one of the jaws can be configured to deliver thermal, electrical, acoustic, or radiofrequency (RF) energy.

In other aspects, a surgical device is provided which includes an end effector having first, second, and third jaws coupled thereto and being movable between open and closed positions. Distal tips of the first, second, and third jaws can directly contact one another in the closed position. The first, second, and third jaws can also define an opening therebetween in the closed position.

The end effector and the jaws can have a variety of configurations. For example, the jaws can be positioned symmetrically about a longitudinal axis of the end effector. In one embodiment, at least one of the jaws can be longitudinally retractable relative to the other jaws. Each jaw can have, for example, a distal tip with a substantially triangular shape. In one embodiment, each jaw can have first and second substantially planar tissue-grasping surfaces. The first and second surfaces can extend at an obtuse angle relative to one another.

In other aspects, the closed jaws can have first, second, and third windows therebetween for accessing the opening. In one embodiment, the jaws can define a substantially cylindrical cross-sectional shape taken along a longitudinal axis extending through the jaws when the jaws are in the closed position. In another embodiment, the first jaw can have first and second engagement surfaces that directly contact a first engagement surface on the second jaw and a first engagement surface on the third jaw, respectively, and the second jaw can have a second engagement surface that directly contacts a second engagement surface on the third jaw.

In other aspects, a method for grasping tissue is provided and includes positioning an end effector having first, second, and third jaws at a first location within a body cavity. The first and second jaws are pivoted to grasp tissue at a first location between the first and second jaws. The method also includes moving the end effector with the tissue grasped between the first and second jaws to a second location within the body cavity, and pivoting the third jaw to grasp tissue at the second location between the third jaw and the first and second jaws. In one embodiment, a portion of the tissue grasped between the first, second, and third jaws can be accessible through a window formed between the first, second, and third jaws, and the method can further include applying a tissue anchor to the accessible portion of the tissue.

In some embodiments, energy can be applied to the grasped tissue. In one embodiment, the method can also include longitudinally retracting the third jaw relative to the first and second jaws.

In other aspects, a method for locating a puncture in tissue is provided, which includes positioning first, second, and third jaws of an end effector around a puncture site in tissue, and closing the first, second, and third jaws to grasp the tissue and occlude blood flow to the puncture. The puncture can be exposed through a window formed between the jaws. In one embodiment, the first, second, and third jaws can be positioned substantially symmetrically around the puncture site in the tissue.

In one embodiment, the end effector can be rotated relative to a handle so as to allow visualization of the puncture. In one embodiment, the method can also include delivering energy to the tissue through at least one of the first, second, and third jaws.

BRIEF DESCRIPTION OF THE DRAWINGS

The invention will be more fully understood from the following detailed description taken in conjunction with the accompanying drawings, in which:

FIG. 7 is an enlarged view of one exemplary jaw of the end effector of FIG. 1;

FIG. 8 is an enlarged view of one exemplary housing of the end effector of FIG. 1;

FIG. 12 is an enlarged view of one exemplary jaw of the end effector of FIG. 10;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices utilizing an end effector having three jaws movably coupled thereto for grasping and/or dissecting tissue. In general, a laparoscopic device is provided having an elongate shaft with an end effector having three movable jaws. The jaws can be configured to grasp tissue and/or to dissect tissue, e.g., spread tissue apart by opening the jaws. In certain embodiments, the use of the three jaws can be particularly advantageous as it can result in less pressure being applied to the tissue by each jaw, as compared to a two-jawed device, thereby reducing the risk of unintentional damage to the tissue. The use of the three jaws can also create a window between the jaws when the jaws are closed, thereby providing access to the tissue. In other embodiments, the use of the three jaws can be advantageous as it allows a more circular opening to be formed in tissue, rather than an elongate slot as would be formed with two jaws. A person skilled in the art will appreciate that, while a laparoscopic device is shown, the concepts described herein can be used in a variety of other surgical devices, including endoscopic devices and other minimally invasive and open surgical devices. For example, the elongate shaft of the device can be flexible, rather than rigid, for insertion through a tortuous body lumen.

Figure 1:
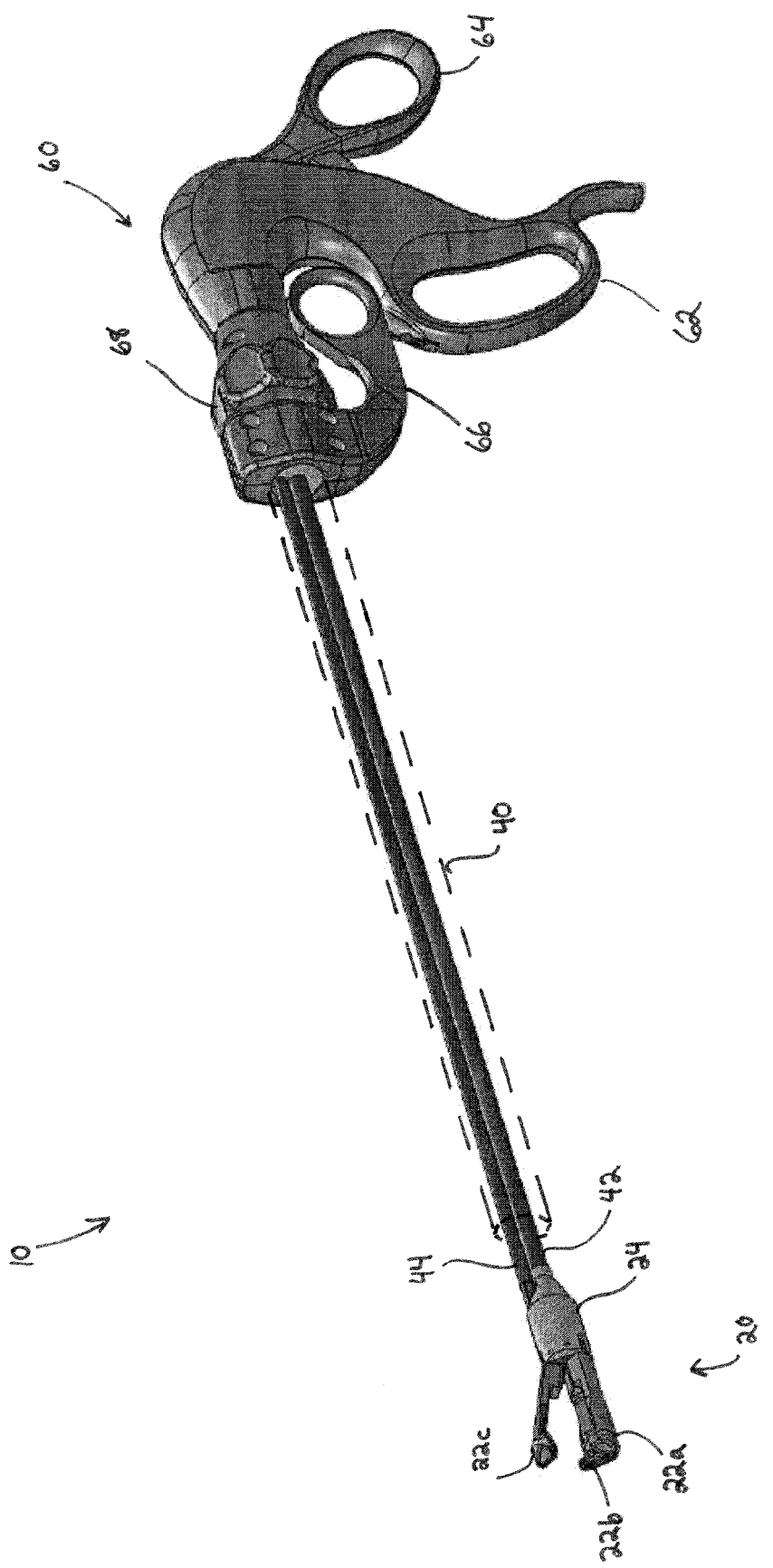
FIG. 1 illustrates a perspective view of one exemplary embodiment of a surgical device having an exemplary three-jawed end effector.

FIG. 1 depicts one exemplary embodiment of a laparoscopic device 10 that includes an end effector 20 having three jaws 22a-c movably coupled thereto. In this embodiment, the end effector 20 is particularly useful for grasping tissue, however in other embodiments, the end effector can be configured to dissect tissue. Surgical devices or instruments utilizing the end effectors described herein can have a number of configurations, but generally can deliver the end effector 20 to an internal surgical site through any opening in a patient's body, whether through a surgical opening (e.g., through a trocar in a percutaneous incision or a purely percutaneous approach without the use of an auxiliary endoscope, trocar, or other access port) or through a natural orifice (e.g., orally, anally, or vaginally). As shown in FIG. 1, the end effector 20 can be disposed at a distal end of an elongate shaft 40 (shown in phantom) and can be operatively coupled to a handle assembly 60. An actuation mechanism 42, 44 can extend through or along the elongate shaft 40 and can transmit actuation of the handle assembly 60 to the end effector 20 to cause various movements, as will be discussed below.

The handle 60 can have a variety of configurations, but is generally configured to be positioned outside the patient's body to facilitate control of the end effector 20. A person skilled in the skill in the art will appreciate that any of the various handle assemblies known in the art can be used including, for example, scissor-grip, pistol-grip, palm-grip, spool style handles, syringe style handles, and various other handle configurations modified in accordance with the teachings herein. An exemplary embodiment of a handle for use with the end effectors described herein is disclosed in U.S. patent application Ser. No. 12/904,280, entitled "Laparoscopic Device with Distal Handle" and filed Oct. 14, 2010, which is hereby incorporated by reference in its entirety.

In the embodiment illustrated in FIG. 1, the handle assembly 60 is generally pistol-shaped and includes a stationary grip 62 extending from a bottom surface of the handle assembly 60. The handle assembly 60 also includes a primary trigger 64, a secondary trigger 66, and a rotatable knob 68, all of which are moveably coupled to the handle assembly 60. As will be discussed in detail below, the primary trigger 64 is pivotally coupled to the handle assembly 60 and can be effective to move a primary actuator 42 longitudinally relative to the shaft 40 or handle assembly 60 to open and close first and second jaws 22a,b of the end effector 20. The secondary trigger 66, which is configured to slide relative to the handle assembly 60, can be effective to move a secondary actuator 44 relative to the shaft 40 or handle assembly 60 to independently open and close and/or translate the third jaw 22c. The rotatable knob 68 is rotatably coupled to the handle assembly 60 and can be effective to rotate the primary and secondary actuators 42, 44 relative to the handle assembly 60 in order to rotate the end effector 20. Though not shown, the handle assembly 60 can include additional or alternative triggers configured to effect various motions of the end effector 20. As will be appreciated by a person skilled in the art, the handle assembly 60 can include, for example, a separate trigger to allow for articulation (e.g., pivoting) of the end effector 20 about the longitudinal axis of the shaft 40. In such a manner, the device 10 can include a "wrist" joint which allows for additional degrees of freedom of the end effector 20.

Figure 2:
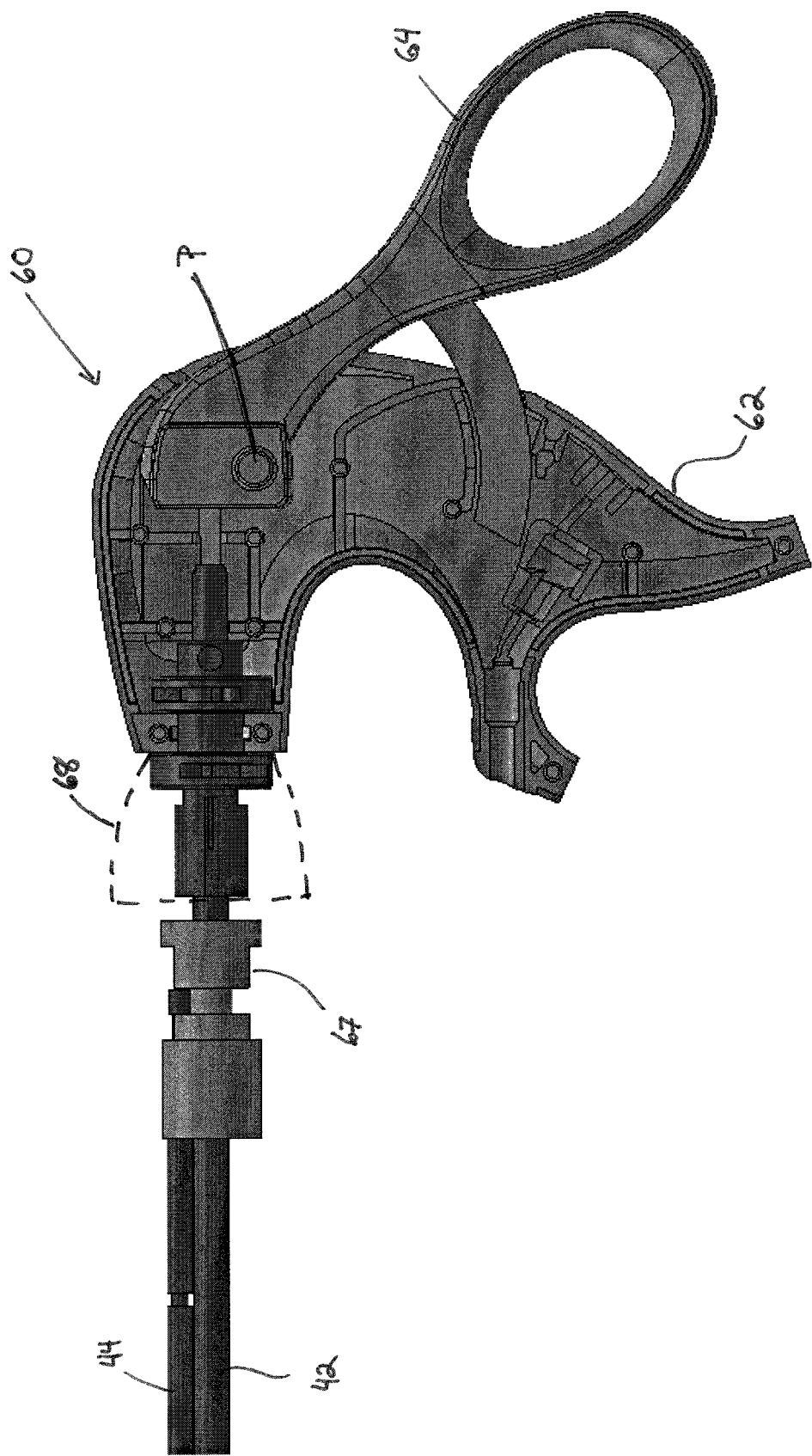
FIG. 2 is a partial cross-sectional view of a proximal portion of the surgical device of FIG. 1, showing a handle and actuation mechanism for controlling the end effector.

As shown in more detail in FIG. 2, the primary trigger 64 can pivot about a pivot point (P) in a direction towards and away from the stationary grip 62. The primary actuator 42 extends proximally within the handle assembly 60 to the couple to the primary trigger 64. In use, the operator can place one or more fingers (e.g., the middle finger) through the stationary grip 62, for example, and manipulate the primary trigger 64 with the thumb to move the primary trigger 64 towards the stationary grip 62, thereby pulling the primary actuator 42 proximally. A spring (not shown) can bias the primary actuator 42 in its distal configuration such that when the primary trigger 64 is released, the spring can return the primary actuator 42 to its unactuated position shown in FIG. 2. As will be appreciated by a person skilled in the art, the primary trigger 64 can also include a locking element that can be securely coupled to a corresponding locking element formed on the stationary grip 62 to allow the user to secure the primary trigger 64, and thus the primary actuator 42 and first and second jaws 22a,b in a given position. Various other locking mechanisms known in the art can also or alternatively be used, including pawl and ratchet mechanisms, gears, etc.

The device 10 can also include a collar 67 (coupled to the secondary trigger 66) that engages the secondary actuator 44 such that proximal movement of the secondary trigger 66 (e.g., a finger loop configured to receive a user's index finger) is effective to move (e.g., slide) the collar 67 relative to the primary actuator 42, thereby pulling the secondary actuator 44 proximally and moving the third jaw 22c, as discussed elsewhere herein.

As discussed above, the handle 60 can additionally include a rotatable knob 68 (shown in phantom in FIG. 2) for rotating the primary and secondary actuators 42, 44 relative to the handle assembly 60. The rotatable knob 68 can include a lumen that receives the proximal end of the primary actuator 42. The lumen can be shaped to allow free slidable movement of the primary actuator 42 along its axis, and to rotationally couple the proximal end of the primary actuator 42 to the knob 68. As a result, when the knob 68 is rotated, a torque is generated which causes rotation of the primary actuator 42, the secondary actuator 44, and the end effector 20. Other rotation mechanisms known in the art can also or alternatively be used, and the rotation mechanism can be disposed anywhere on the handle assembly 20 and/or the shaft 40 for rotating the end effector 20 relative to the handle assembly 60.

The shaft 40 can also have a variety of configurations, but generally extends distally from the handle assembly 60 and defines a lumen through which the actuator(s) 42, 44 can extend. The proximal end of the shaft 40 can be integral with the handle assembly 60 or it can be fixedly or removably coupled to the handle assembly 60. Additionally, the shaft 40 can be configured to move (e.g., rotate or move longitudinally) relative to the handle assembly 60.

A person skilled in the skill in the art will appreciate that any of the various shafts for laparoscopic, endoscopic, percutaneous, and other minimally invasive surgical devices known in the art can be modified in accordance with the teachings herein. By way of non-limiting example, the elongate shaft 40 can be rigid and configured to be inserted through an access port or surgical incision. Alternatively, in some embodiments, at least a portion of the elongate shaft 40 can be flexible or semi-flexible to allow the shaft 40 to be inserted into a patient translumenally, e.g., through a natural orifice or an endoscope. The flexibility of the shaft 40 can vary along its length and the shaft 40 can be formed from one or more components that are mated together. For example, a flexible elongate shaft 40 can be formed from a friction reducing flexible outer sheath having a flat coil wire extending therethrough.

The primary and secondary actuators 42, 44 can also have a variety of configurations, but in the depicted embodiment, the actuators 42, 44 extend distally from the handle assembly 60 to the end effector 20 and are configured to actuate the end effector 20. One skilled in the art will appreciate that the actuators 42, 44 can have any number of configurations, shapes, and sizes depending at least in part on the configuration of the shaft 40, the end effector 20, the handle assembly 60, and the motion to be effected. For instance, the actuators 42, 44 can extend through the elongate shaft 40 and connect terminally to the end effector 20. As described herein, actuation of the handle assembly 60 (e.g., movement of the primary or secondary triggers 64, 66 or the rotatable knob 68) can impart motion to the actuators 42, 44 or shaft 40, thereby resulting in movement of the end effector 20.

The primary and secondary actuators 42,44 can be made from any suitable material. By way of non-limiting example, the actuators 42, 44 can be a rod, cable, or metal wire (e.g., a multi-layered steel cable, such as a tri-layered steel cable). The actuators 42, 44 can be rigid or can be formed from a flexible or semi-flexible material, such as a nickel-titanium alloy or stainless steel, which permits the actuators 42, 44 to transmit torque by rotation without taking a cast, and with minimal whipping. The actuators 42, 44 can also have a sufficiently large diameter to transmit longitudinal force and torque to the distal end of the actuators 42, 44, yet not so large that the actuators 42, 44 are prevented from flexing if the elongate shaft 40 is passed through a tortuous lumen.

In the embodiment depicted in FIGS. 1-8, the primary and secondary actuators 42, 44 are rigid rods (they can be the same or different as one another) that extend between the end effector 20 and the handle assembly 60. As will be discussed in detail below, the primary actuator 42 can be coupled at its distal end to the first and second jaws 22a,b and can extend proximally into the housing assembly 60 to be operatively coupled to the primary trigger 64. The secondary actuator 44 can be coupled at its distal end to the third jaw 22c and can extend proximally through the shaft 40 to the secondary trigger 66. In such a manner, actuation of the primary trigger 64 can be transmitted to the first and second jaws 22a,b via longitudinal (e.g., axial) movement of the primary actuator 42 through the shaft 40, while actuation of the secondary trigger 66 can be transmitted to the third jaw 22c via longitudinal (e.g., axial) movement of the secondary actuator 44 through the shaft 40. As discussed above, rotation of the knob 68 can be effective to rotate the primary and secondary actuators 42,44, thereby resulting in rotation of the end effector 20.

The end effector 20 can also have a variety of configurations for performing various procedures, such as grasping or dissecting tissue. As shown in FIG. 1, the end effector 20 can include, for example, a housing 24 and three jaws 22a-c for engaging tissue therebetween. As discussed in detail below, each of the jaws 22a-c can be movably coupled to the housing 24 such that the movement of the actuators 42, 44 coupled to each of the respective jaws 22a-c can be effective to actuate the jaws 22a-c between variety of positions relative to one another so as to enable the end effector 20 to grasp tissue.

Figure 3:
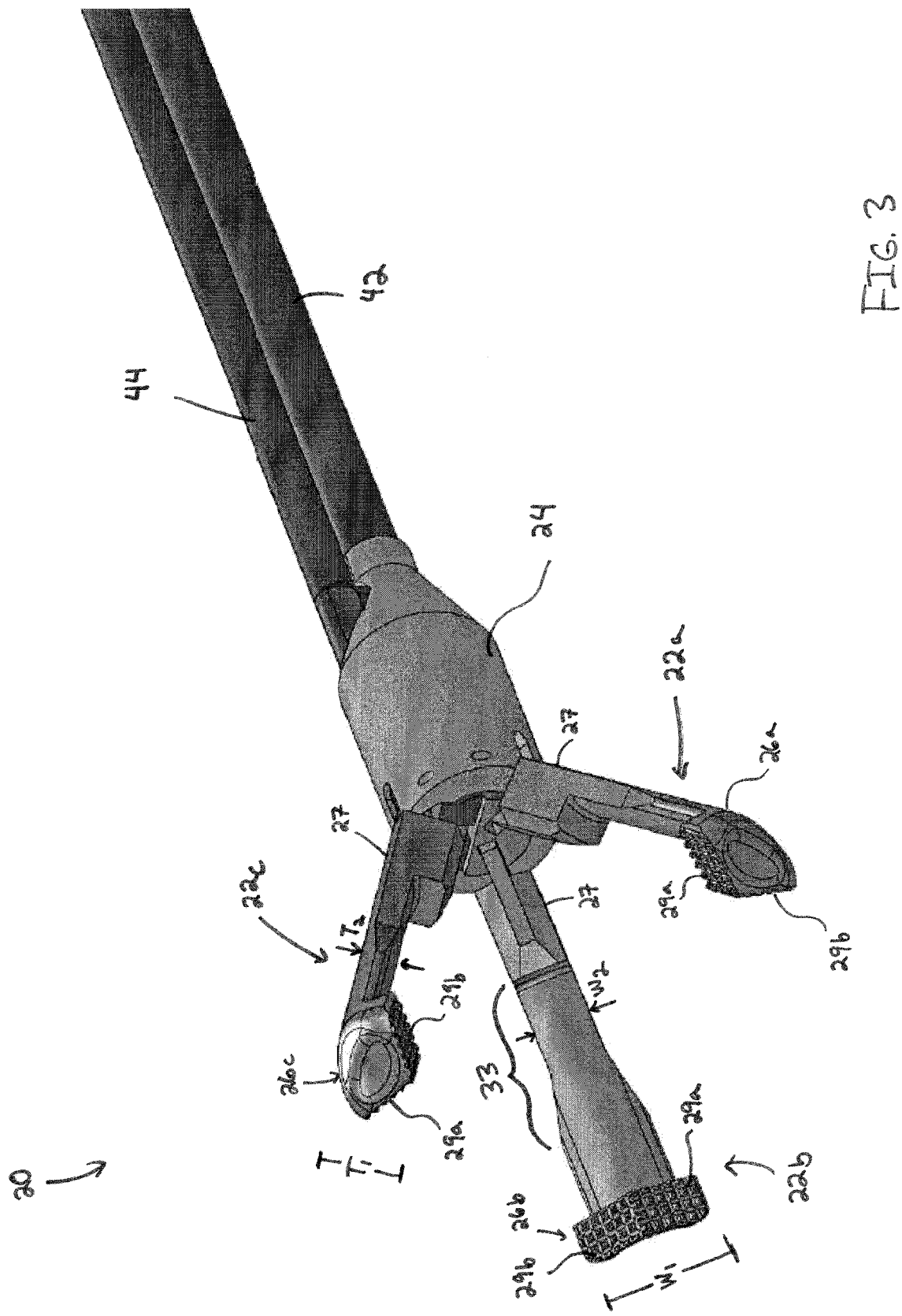
FIG. 3 is a perspective view of the end effector of FIG. 1, depicting the end effector in an open configuration.
Figure 4:
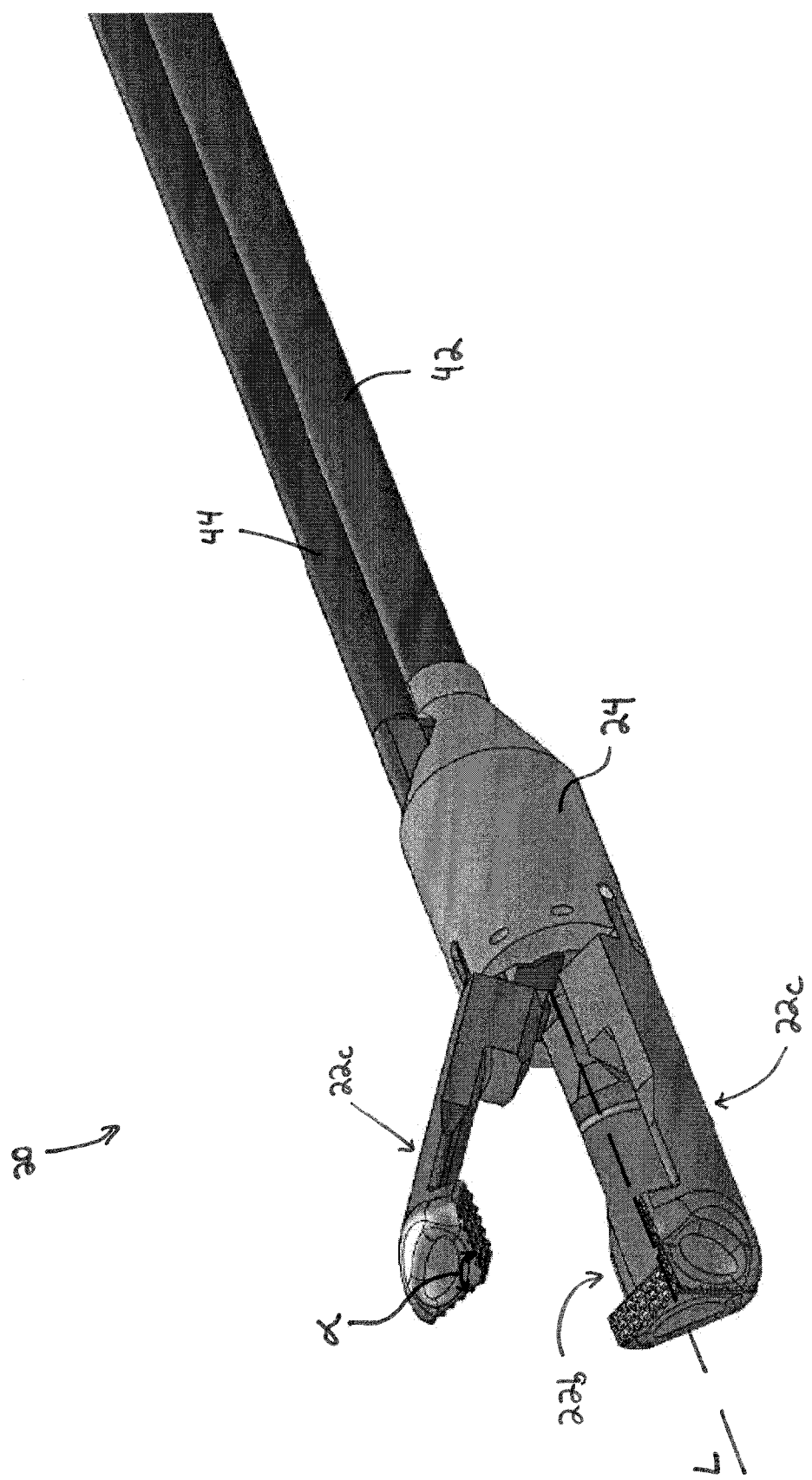
FIG. 4 is a perspective view of the end effector of FIG. 1, depicting the end effector in a semi-closed configuration.
Figure 5:
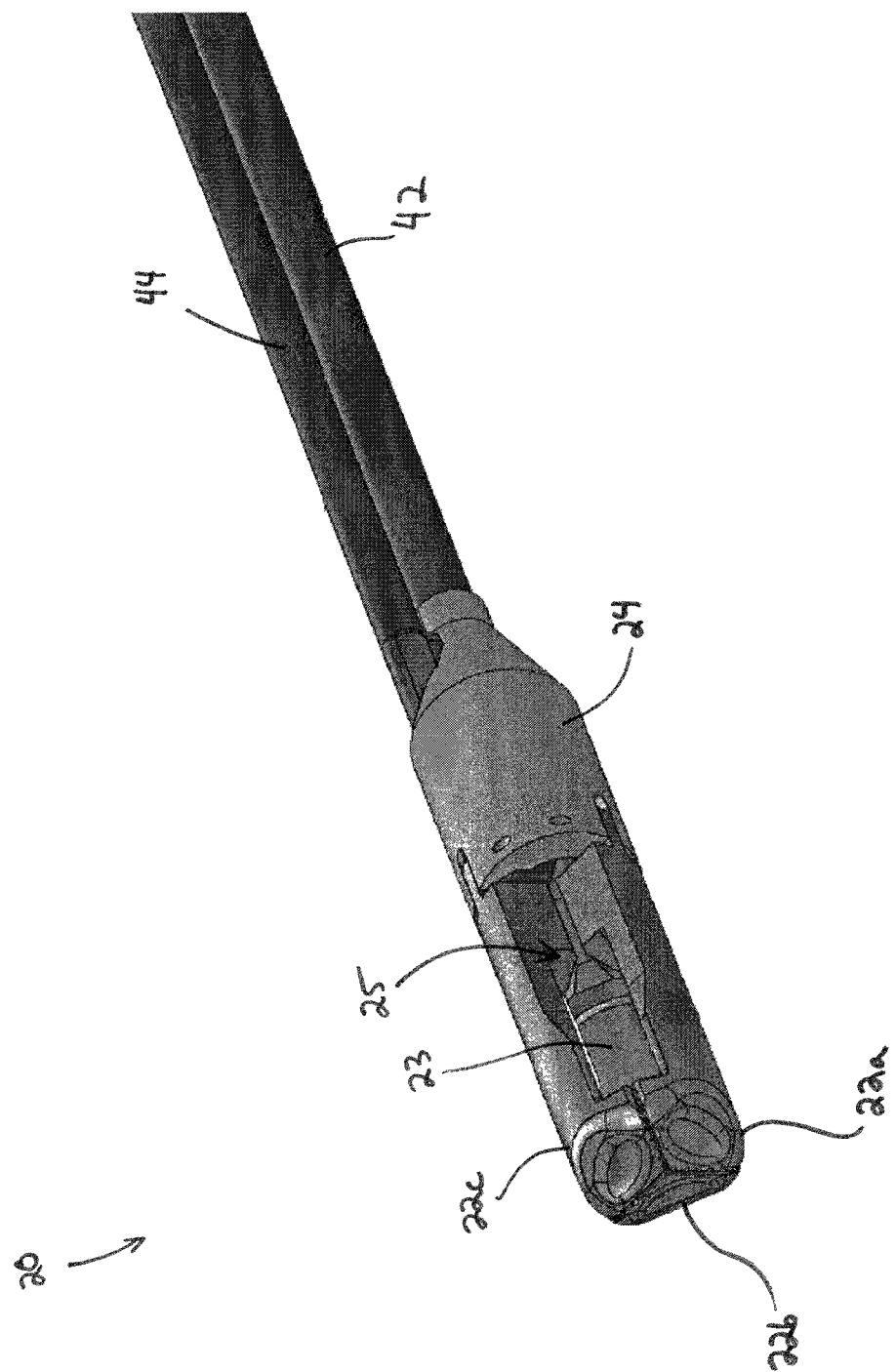
FIG. 5 is a perspective view of the end effector of FIG. 1, depicting the end effector in a closed configuration.

Taken together, in the embodiment depicted in FIGS. 1-8, actuation of the primary and secondary actuators 42, 44 can allow for the jaws 22a-c to move between an open position in which the distal ends 26a-c of the three jaws 22a-c are spaced apart from one another (as shown in FIG. 3) and a closed position in which the distal ends 26a-c directly contact one another (as shown in FIG. 5). Further, the primary and secondary actuators 42, 44 can be effective to move the jaws between various alternative or intermediate positions. For example, as shown in FIG. 4, the end effector 20 can have a semi-closed position in which the first and second jaws 22a,b are closed and aligned along the longitudinal axis (L) of the end effector 20, while the third jaw 22c is open and angularly disposed relative to the longitudinal axis (L) of the end effector 20. As will be appreciated by a person skilled in the art, in some embodiments, the three jaws 22a-c can be selectively biased to one of their open position or closed position.

As will be appreciated by a person skilled in the art, the first and second jaws 22a,b can be coupled to the primary actuator 42 in a variety of manners such that actuation (e.g., longitudinal movement) of the primary actuator 42 is effective to move the first and second jaws 22a,b between an open position in which the longitudinal axis of the first and second jaws 22a,b are angularly disposed relative to the longitudinal axis (L) of the end effector 20 and a closed position in which the longitudinal axis of the jaws 22a,b are substantially aligned along the longitudinal axis of the end effector 20. Similarly, the third jaw 22c can be coupled to the secondary actuator 44 such that actuation (e.g., longitudinal movement) of the secondary actuator 44 can be effective to move the third jaw 22c between a position in which the axis of the third jaw 22c is angularly disposed relative to the longitudinal axis of the shaft 40 and a position in which the axis of the third jaw 22c is substantially aligned along the longitudinal axis of the end effector 20. In FIG. 4, for example, the first and second jaws 22a,b are shown in a position aligned along the longitudinal axis of the end effector 20. The third jaw 22c, on the other hand, is angularly disposed relative to the longitudinal axis of the end effector 20.

Figure 6:
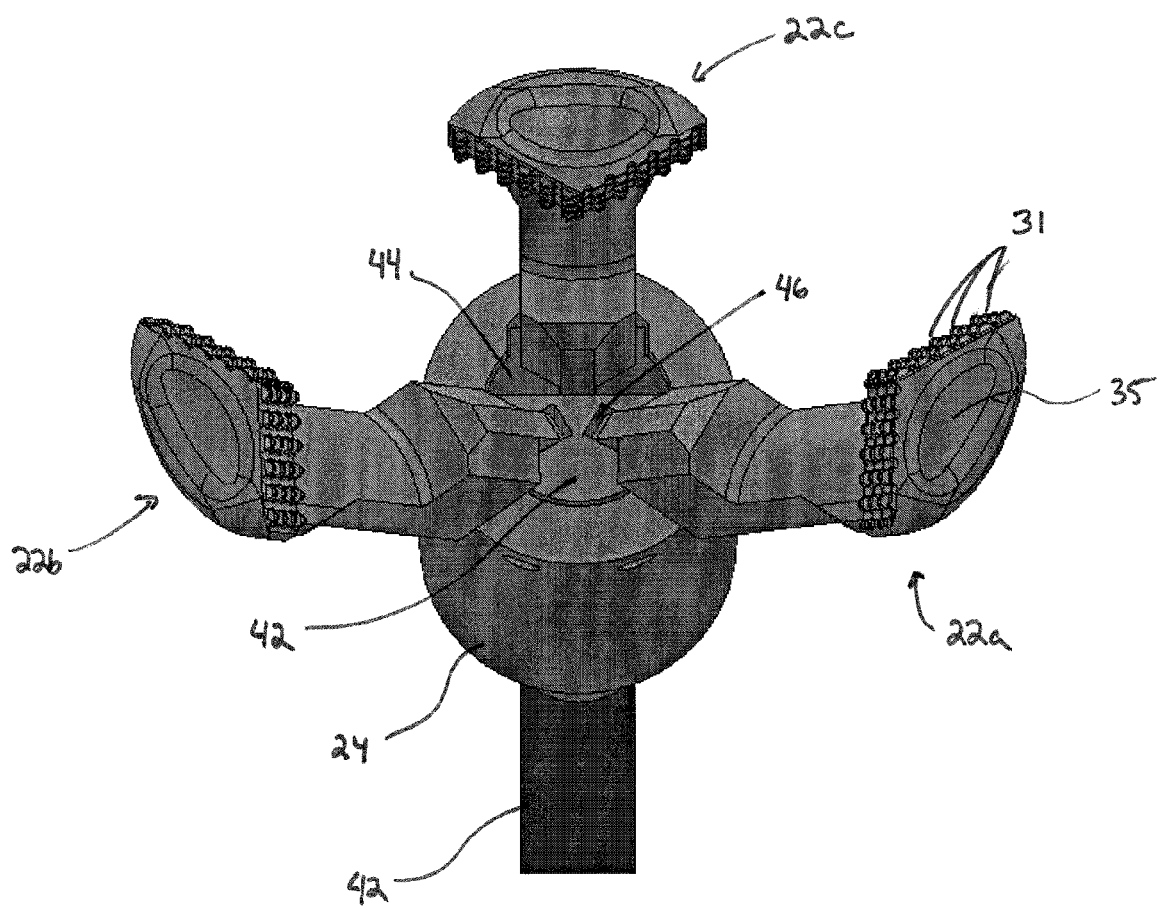
FIG. 6 is a distal end view of the distal end of the end effector of FIG. 1.

With specific reference now to FIGS. 6-8, the distal end of the primary actuator 42 extends through a central channel 28 of the housing 24 and includes two cavities 46 formed in its distal most end, each of which is configured to partially receive a proximal extension 30 of each of the jaws 22a,b. Similarly, the distal end of the secondary actuator 44 extends through the housing 24 and includes a cavity (not shown) formed in its distal most end that is configured to partially receive a proximal extension 30 of the third jaw 22c. The housing 24 can also include three distal channels 32, each of which is configured to partially receive the proximal extension of one of the jaws 22a-c. As shown in FIG. 8, the housing 24 can additionally include a proximal shoulder 38, which can be effective to prevent proximal disengagement of the primary and secondary actuators 42, 44 from the housing through abutment, for example, with the proximal extension 30 of the jaws 22a-c or a corresponding shoulder formed on the primary and secondary actuators 42, 44.

Though the following description specifically refers to one exemplary embodiment of the coupling of the first jaw 22a to the primary actuator 42 and the end effector 20, a person skilled in the art will appreciate that the second and third jaws 22b,c can be similarly coupled to their respective actuators 42,44. As best shown in FIG. 7, the proximal extension 30 of the first jaw 22a can include a superior, circular bore 34 and an inferior, non-circular bore 36, each of which is configured to receive a rivet therethrough for coupling the first jaw 22a to the housing 24 of the end effector 20 and the primary actuator 42, respectively. For example, the inferior bore 36 can receive a first rivet (not shown) extending through the cavity 46 in the distal end of the primary actuator 42 while the superior bore 34 can receive a second rivet (not shown) extending through the distal channel 32 of the housing 24. In such a manner, distal movement of the primary actuator 42 can be effective to "push" the first jaw 22a distally (e.g., by the first rivet engaging the distal end of the non-circular bore 36), thereby forcing the first jaw 22a to pivot about the second rivet extending through the superior bore 34, and hence, moving the first jaw 22a between a closed position in which its axis is substantially aligned along the longitudinal axis of the end effector 20 and an open position in which the axis of the first jaw 22a is angularly disposed relative to the longitudinal axis of the end effector 20. Conversely, proximal movement of the primary actuator 42 can pull the first jaw 22a proximally, and thus, force the first jaw 22a to pivot (e.g., in an opposite direction from above) from an open position in which its axis is angularly disposed relative to the longitudinal axis of the end effector 20 to a position in which its axis substantially aligned along the longitudinal axis of the end effector 20.

Accordingly, each of the first and second jaws 22a,b can be coupled to the distal end of the primary actuator 42 through rivets such that longitudinal (i.e., axial) movement of the primary actuator 42 is effective to move the first and second jaws 22a,b between their open and closed positions. Similarly, the third jaw 22c can be coupled to the distal end of the secondary actuator 44 such that longitudinal movement of the secondary actuator 42 is effective to move the third jaw 22c between its configuration in the open and closed positions.

Referring again to FIGS. 3-5, the jaws 22a-c are shown in further detail. The jaws 22a-c can have a variety of configurations but generally include a proximal end 27 coupled to one of the primary or secondary actuators 42, 44 and a distal end 26a-c configured to contact tissue and/or the distal ends of the other jaws. As will be appreciated by a person skilled in the art, though the jaws 22a-c are depicted as being substantially identical, each of the jaws 22a-c can differ and can have a variety of configurations that enables the jaws to grasp tissue therebetween.

The jaws 22a-c can be disposed in variety of positions around the longitudinal axis (L) of the end effector 20. As will be appreciated by a person skilled in the art, the disposition of the jaws about the longitudinal axis can affect their relative movements. By way of example, the first, second, and third jaws 22a-c can be positioned symmetrically about the longitudinal axis of the end effector 20, as shown in FIG. 3. Such a configuration can allow for pivoting movement of each of the three jaws 22a-c along a different plane relative to the other two jaws. Alternatively, the jaws 22a-c can extend from the housing 24 asymmetrically. For example, in one embodiment, the first and second jaws 22a,b can extend distally from the housing 24 such that their actuation results in movement of the first and second jaws 22a,b in the same plane, while the third jaw 22c can move in a plane orthogonal to the plane of movement of the first and second jaws 22a,b.

As will be appreciated by a person skilled in the art, the distal ends 26a-c of the jaws 22a-c can have a variety of configurations depending on their relative positioning about the longitudinal axis (L) of the end effector 20 and their intended use. For example, the distal ends 26a-c of each of the jaws 22a-c can have a variety of shapes so as to engage one another when in the closed position. As shown in FIGS. 3-5, each of the jaws 22a-c includes a distal-most tip with a substantially triangular cross-section having two substantially planar engagement surfaces 29a,b. When the jaws 22a-c move from an open position, as shown in FIG. 3, to the closed position as shown in FIG. 5, the planar engagement surfaces 29a,b of each jaw can engage the corresponding planar engagement surface of the adjacent jaw. By way of example, one of the engagement surfaces 29b of the first jaw 22a can directly contact one of the engagement surfaces 29a of the second jaw 22b when the jaws 22a-c are in the closed position, while the other engagement surface 29a of the first jaw 22a can directly contact one of the engagement surfaces 29b of the third jaw 22c. Similarly, the engagement surface 29b of the second jaw 22b not in contact with the first jaw 22a can engage the engagement surface 29a of the third jaw 22c not in contact with the first jaw 22a. In such a manner, the jaws 22a-c in their closed positions can nest with one another, thereby resulting in an end effector having a substantially cylindrical shape, for example, as shown in FIG. 5. As will be appreciated by a person skilled in the art, the shape and size of the end effector 20 in the closed position can vary depending on the configuration and relative positioning of the jaws 22a-c and on the shape and size of the access port and the surgical site. By way of non-limiting example, an end effector 20 for insertion into the bowel can have a diameter of about 10 mm, while an end effector 20 for use with smaller structures (e.g., gallbladder, appendix) can have a diameter of about 5 mm.

The substantially planar engagement surfaces 29a,b can have a variety of configurations. By way of example, the two planar engagement surfaces 29a can extend at a variety of angles relative to one another. For example, as depicted in FIGS. 3-5, each engagement surface 29a,b in the pair on each jaw 22a-c extends at an obtuse angle ($\alpha$) relative to the other engagement surface in the pair on the same jaw. As will be appreciated by a person skilled in the art, in a configuration in which the jaws 22a-c are disposed symmetrically about the longitudinal axis, the engagement surfaces on each jaw 22a-c can extend at an angle of about 120° relative to the other engagement surface on the same jaw. This angle can vary, however, depending on the positioning of the jaws 22a-c relative to one another. For example, in an embodiment in which the first and second jaws 22a,b are both configured to move in a first plane while the third jaw 22c is configured to move in a second plane orthogonal to the first plane as discussed above, one engagement surface 29a of the first jaw 22a can approximately extend at a right angle relative to the other engagement surface 29b (and similarly for the engagement surfaces of the second jaw 22b), while the third jaw 22c can have a single planar engagement surface (i.e., two engagement surfaces extending 180° relative to one another).

The substantially planar engagement surfaces 29a,b can also include surface features formed thereon to facilitate engagement between the jaws 22a-c. For example, as shown in FIG. 7, the planar engagement surfaces 29a-b can include a plurality of protrusions 31 that nest between the protrusions 31 formed on the corresponding engagement surfaces 29a,b of the adjacent jaw when the jaws 22a-c are in the closed position. As will be appreciated by a person skilled in the art, the protrusions 31 formed on the engagement surfaces 29a,b can also be configured to facilitate engagement of tissue disposed between the jaws 22a-c so as to prevent tissue engaged thereto from slipping from between the jaws 22a-c when in the closed position.

With specific reference now to FIG. 5, though the distal ends 26a-c of the jaws 22a-c are in direct contact with one another, the jaws 22a-c can be configured to define a cavity therebetween in the closed position. For example, the jaws 22a-c can include an opening 23 between the jaws 22a-c extending along the longitudinal axis of the end effector 20. Additionally, the jaws 22a-c can further be configured to include one or more windows 25 that provide access to the opening 23.

As will be appreciated by a person skilled in the art, the jaws 22a-c can have a variety of configurations so as to define a central opening 23 and windows 25 providing access thereto. By way of non-limiting example, the jaws 22a-c can bow outwardly and/or the intermediate portions of the jaws 22a-c (i.e., the portion of a jaw between its proximal and distal ends) can vary along their length or include a cut-out to create a cavity between the jaws 22a-c. Further, each of the jaws 22a-c can be shaped so as to at least partially define windows 25 extending axially to the central opening 22.

As shown in FIGS. 3-5, for example, each of the jaws 22a-c is shaped so as to define a central opening 23 and windows 25 providing access thereto. Each of the jaws 22a-c includes an intermediate portion 33 between the distal and proximal ends having a reduced thickness (i.e., radial dimension) relative to the distal and proximal ends of the jaws 22a-c. That is, the intermediate portion 33 of the jaw 22c, for example has a thickness ($T_2$) that is less than the thickness ($T_1$) of the distal end 26c and proximal end 27. As a result, the intermediate portions 33 of the jaws 22a-c are spaced a distance from the longitudinal axis (L) when the jaws 22a-c are in the closed position, unlike the distal ends 26a-c which come together at the longitudinal axis. Further, each of the jaws 22a-c has a width that flares at the distal end 26a-c of its jaw 22a-c. That is, the intermediate portion of the jaw 22b, for example, has a width ($W_2$) that is less than the width ($W_1$) of the distal end 26b. Accordingly, the inner radial surface of the intermediate portions 33 of the jaws 22a-c can define an opening 23 therebetween, while the decreased width ($W_1$) of the intermediate portions can provide windows 25 between adjacent jaws that extend axially into the opening 23.

The shape of the distal ends of the jaws 22*a-c* can also vary depending, for example, on the intended use of the device. By way of non-limiting example, in an embodiment in which the end effector 20 is used primarily to grasp tissue, the jaws 22*a-c* can be configured to minimize damage and/or avoid accidentally piercing tissue at the surgical site. As shown in FIGS. 3-5, the jaws 22*a-c* can include substantially triangular atraumatic distal ends 26*a-c* having a blunt distal most surface 35. As will be appreciated by a person skilled in the art, the distal most surface 35 of the jaws 22*a-c* can be planar or even rounded so as to minimize risk of trauma. As discussed in detail below with reference to FIG. 9, however, in an embodiment in which the end effector can be used for grasping as well as spreading tissue, the distal ends can alternatively have a pointed configuration so as to facilitate insertion through tissue.

In some embodiments, the end effector 20 can be configured to deliver energy to tissue in contact therewith. Additionally or in the alternative to the tissue fasteners discussed otherwise herein, at least one of the jaws 22*a-c* can be configured to deliver energy to tissue secured between the jaws 22*a-c* so as to secure the tissue and/or close (e.g., cauterize) a tissue puncture. By way of example, one of the jaws 22*a-c* can include one or more electrode(s) on a tissue-contacting surface of the jaws for applying energy to the tissue. The electrode(s) can be configured to contact the tissue when disposed between the jaws 22*a-c* of the end effector 20.

As will be appreciated by a person skilled in the art, the electrode(s) can have various configurations depending on the energy to be applied. By way of non-limiting example, thermal energy, electrical energy, acoustic energy (e.g., ultrasonic), and/or radiofrequency (RF) can be applied by the electrode(s) to the tissue. Further, the skilled artisan will appreciate that the treatment parameters (e.g., power, energy, delivery time, frequency, wave pattern) and the physical parameters of the energy delivery system (e.g., the number, diameter, spacing, and location of the electrodes) can be optimized to secure the tissue, close (e.g., cauterize) a tissue puncture, and/or provide another treatment. The skilled artisan will also appreciate that the surgical device can include an energy source operatively coupled to the electrode(s) to activate the one or more electrode(s). By way of example, the energy source can be a battery disposed within the handle assembly 60, or the device 10 can be adapted to couple to an external energy source, such as a generator or an outlet. Further, the device 10 can include a mechanism to activate the delivery of energy by the electrode(s), such as a button or dial disposed on the handle assembly 60.

Figure 9A:
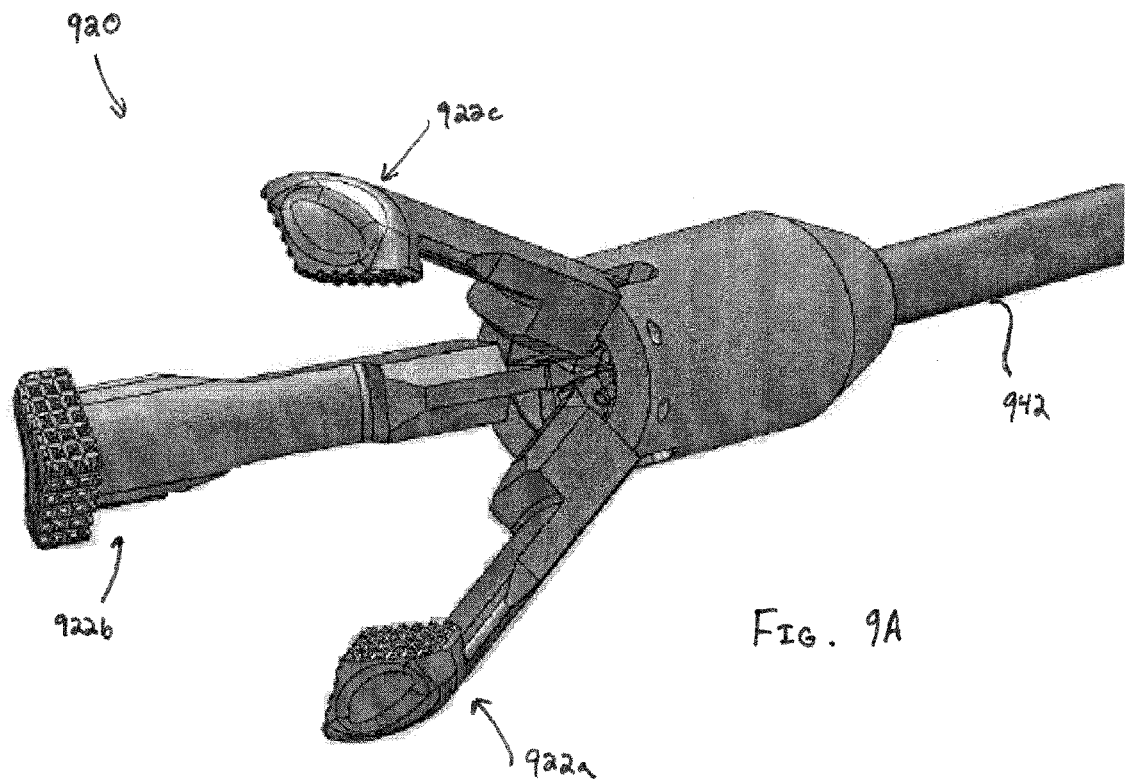
FIG. 9A is a perspective view of the distal end of another exemplary embodiment of a surgical device having an exemplary three-jawed end effector, depicting the end effector in an open configuration.
Figure 9B:
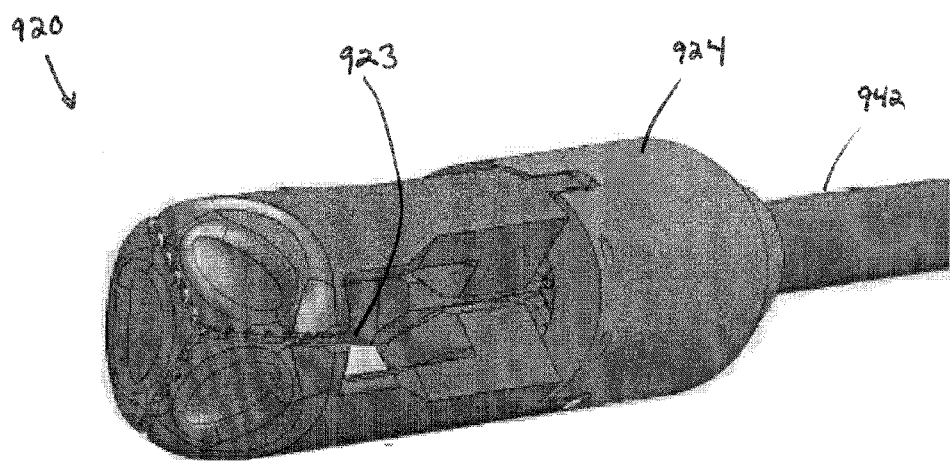
FIG. 9B is a perspective view of the distal end of the end effector of FIG. 9A, depicting the end effector in an open configuration.

With reference now to FIGS. 9A and 9B, another exemplary embodiment of an end effector according to the teachings herein is depicted. The end effector 920 is substantially similar to that described above with reference to FIGS. 1-8, in that the end effector 920 includes three jaws 922*a-c* movably coupled to the housing 924 and extending distally therefrom. As above, each of the jaws 922*a-c* is movable between an open position in which the distal ends of the three jaws 922*a-c* are spaced apart from one another, and a closed position in which the distal ends directly contact one another and define an opening 923.

The end effector 920 differs from the end effector 20 described above, however, in that a single actuator 942 is effective to control the actuation of the three jaws 922*a-c*. Thus, whereas a secondary actuator 44 could independently actuate the third jaw 22*c* in the embodiment depicted in FIG. 1, for example, each of the jaws 922*a-c* is operatively coupled to a single actuator 942 such that its actuation results in synchronized movement of the three jaws 922*a-c* from an open position in which the distal ends of the three jaws 922*a-c* are spaced apart from one another, as shown in FIG. 9A, to a closed position in which the distal ends directly contact one another, as shown in FIG. 9B. As will be appreciated by a person skilled in the art, the handle assembly (not shown) need not therefore include, for example, a secondary trigger 66 for controlling independent actuation of the third jaw 22*c* as described above with reference to FIGS. 1-8, as each of the jaws 922*a-c* can move in concert via the actuation by a user of a single trigger (not shown).

In use, the various devices disclosed herein can be delivered to an internal surgical site through a natural orifice or a surgical incision and can be effective to grasp and/or dissect tissue. With reference to the embodiment depicted in FIGS. 1-8, for example, the end effector 20 disposed at the distal end of the elongate shaft 40 can be positioned at a surgical site. With the three jaws 22*a-c* in the open position, the end effector 20 can be advanced to position the tissue between the jaws 22*a-c*. The primary and secondary triggers 64, 66 can then be actuated to move the three jaws to their closed position, thereby grasping the tissue between the jaws 22*a-c*. Relative to a two-jawed grasping device, the use of an end effector having three jaws in accord with the teachings herein can be particularly advantageous in that the three jaws spread out the pressure necessary to grasp the target tissue. As a result, less pressure can be applied to the tissue by each jaw in order to securely grasp the tissue therebetween, thereby reducing the risk of damage to the tissue.

In one embodiment, use of the three-jawed end effector 22*a-c* can be particularly advantageous for locating a puncture site in tissue. Unlike two-jawed graspers which grasp along a line (i.e., the two jaws move in a single plane), and thus, must be precisely aligned with a puncture site in order to capture or occlude a bleeding vessel, a three-jawed end effector in accord with the teachings herein can improve the ability of surgeons to locate and seal a puncture site. By way of example, the three jaws can enclose a wider tissue target area relative to a two-jawed device and can effectively enclose the tissue puncture site by grasping tissue around the circumference of the puncture.

In one embodiment, the three jaws 22*a-c* of the end effector 20 can be positioned around a probable puncture site in tissue and can be actuated to move the three jaws 22*a-c* to the their closed position such that the tissue surrounding the puncture site is grasped therebetween. Grasping the tissue around the circumference of the puncture site can be effective to stop the flow of blood out of the puncture site and can allow the user to pinpoint the location the puncture site. Advantageously, after actuating the end effector 20 to its closed position such that the tissue containing the puncture is engaged within the opening 23 between the three jaws 22*a-c*, the windows 25 can provide an exit that allow the puncture site to be exposed (e.g., pop out) through a window 25 between adjacent jaws.

By way of example, once the end effector 20 has been actuated to engage and surround a tissue site containing a puncture, the end effector 20 can be rotated to allow visualization of the puncture site that is exposed through the window 25. At this point, for example, any variety of tissue anchors (e.g., sutures, staples, clamps, clasps, etc.) known in the art can be applied to the exposed tissue to seal the puncture and/or prevent further bleeding. In one embodiment in which an electrode disposed on a tissue contacting surface of the jaws 22*a-c* can be energized, or at least one of the jaws 22*a-c* can act as an electrode, the user can elect to deliver energy to seal (e.g., cauterize) the puncture. For example, an electrode, operating in either a bipolar or monopolar mode, can deliver RF energy to the grasped tissue such that the puncture site is sealed.

In one embodiment, independent actuation of the third jaw 22c can enable the end effector 20 to be moved after the first and second jaws 22a,b have already grasped tissue therebetween. By way of example, the end effector 20 can be positioned within a body cavity and, with the jaws in the open configuration, advanced to a surgical site. The first and second jaws 22a,b can then be actuated (e.g., pivoted) to grasp the tissue therebetween. After securing the tissue between the first and second jaws, the end effector 20 can be moved to a second location (e.g., adjacent the first site) such that the third jaw can be actuated to grasp additional tissue between the third jaw 22c and the first and second jaws 22a,b. In such a manner, the end effector 20 having an independently-actuated third jaw 22c can grasp a larger tissue area relative to an end effector having three jaws actuated simultaneously. As will be discussed in detail below, the third jaw 22c can also be proximally retracted relative to the first and second jaws 22a,b, depending on the needs of the surgeon (e.g., to better visualize the surgical site).

As discussed above, a portion of the tissue (e.g., a puncture site) retained within the opening between the three jaws 22a-c can thus be exposed through a window between adjacent jaws such that a tissue anchor can be applied to the exposed tissue. Additionally or in the alternative, energy can be applied to seal the puncture site.

As noted above, an end effector which can be used for both grasping and dissecting tissue can have a different configuration from an end effector that is primarily used to grasp tissue. Though the end effectors described above can also be used for dissection, the shape of the distal ends 26a-c of the jaws 22a-c can be modified, for example, so as to facilitate insertion through tissue. With specific reference now to FIG. 10, an exemplary embodiment of a laparoscopic device 1010 that is particularly useful for dissecting tissue is depicted. The device 1010 includes an end effector 1020 having three jaws 1022a-c movably coupled thereto and configured to move between a configuration in which their distal ends 1026a-c are spaced apart from one another and a configuration in which their distal ends 1026a-c directly contact one another. As above, the end effector 1020 can be operatively coupled to a handle assembly 1060 via primary and secondary actuators 1042, 1044 to transmit actuation of the handle assembly 1060 to the end effector 1020 to cause various movements thereof, as will be discussed below.

As will be appreciated by a person skilled in the art, the handle assembly 1060 and the actuators 1042, 1044 can have various configurations as discussed otherwise herein. In the embodiment depicted in FIG. 10, for example, the handle assembly 1060 includes a stationary grip 1062, a primary trigger 1064 for controlling movement of the primary actuator 1042, a secondary trigger 1066 for controlling movement of the secondary actuator 1044, and a rotatable knob 1068 for rotating the end effector 1020 relative to the handle assembly 1060.

As in the above-described device 10, the end effector 1020 can be configured such that each of the first and second jaws 1022a,b can move between an open position in which their distal ends 1026a,b are spaced apart from one another and a closed position in which their distal ends 1026a,b directly contact one another. The end effector 1020 differs from that discussed above with reference to FIG. 1, however, in that the independently-controlled third jaw 1022c, though movably coupled to the end effector 1020, maintains a fixed orientation relative to the longitudinal axis of the end effector 1020. Rather than pivot, the third jaw 1022c is instead configured to retract and extend axially relative to the housing 1024.

As will be appreciated by a person skilled in the art, the housing 1024 can have a variety of configurations that allow for the axial movement of the third jaw 1022c. By way of example, though the central opening (not shown) of the housing 1024 can include a proximal shoulder (not shown) that prevents movement of the proximal extension 1030 of the jaws 1022a,b proximally beyond the housing 1024 as discussed above with reference to the housing 24 of FIG. 8, the central opening can be shaped so as to allow for the slidable movement of the secondary actuator 1044 and/or at least a portion of the third jaw 1022c through the housing 1024. Alternatively, a separate opening (e.g., slot, bore, etc.) can extend through the housing 1024 and can be configured to slidably receive the secondary actuator 1044 and/or at least a portion of the third jaw 1022c. In such a manner, proximal movement of the secondary actuator 1044 relative to the housing 1024 can be effective to pull the third jaw 1022c proximally, thereby sliding a proximal portion of the third jaw 1022c within the opening in the housing 1024. Conversely, distal movement of the secondary actuator 1044 can be effective to push the third jaw 1022c distally from the opening of the housing 1024 to an extended position.

Figure 11A:
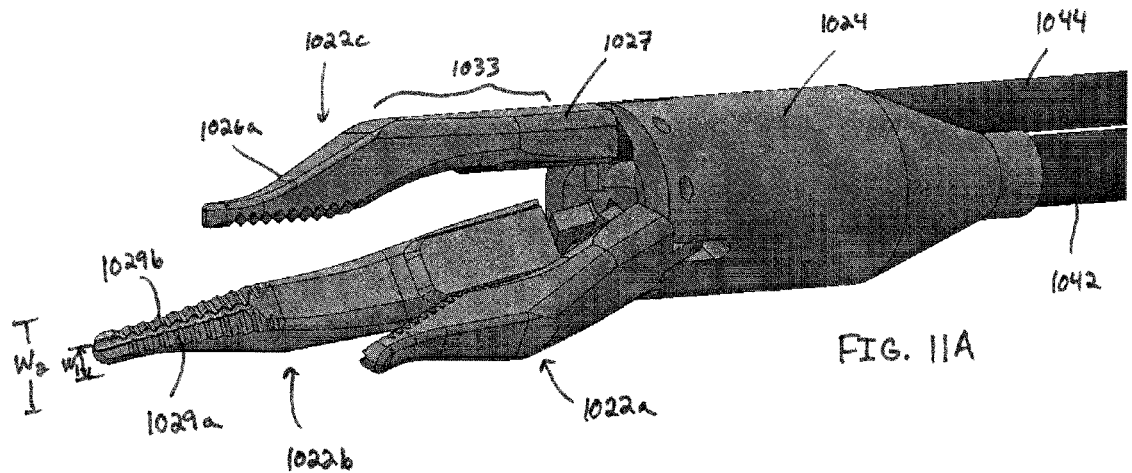
FIG. 11A is a perspective view of the end effector of FIG. 10, depicting the end effector in an open configuration.
Figure 11B:
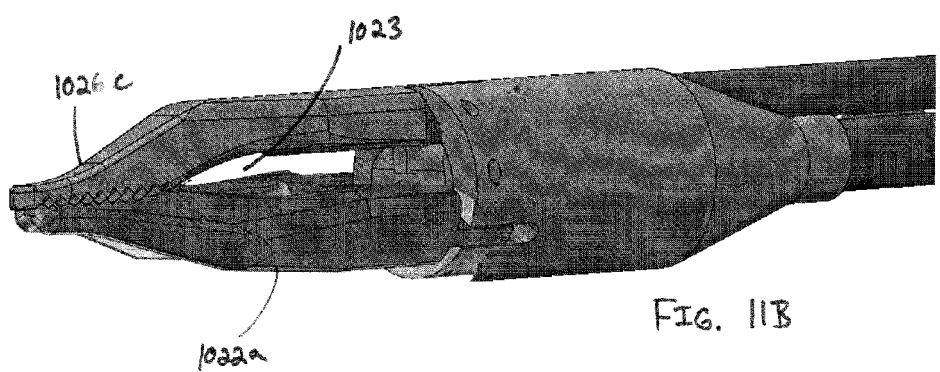
FIG. 11B is a perspective view of the end effector of FIG. 10, depicting the end effector in an open configuration.
Figure 11C:
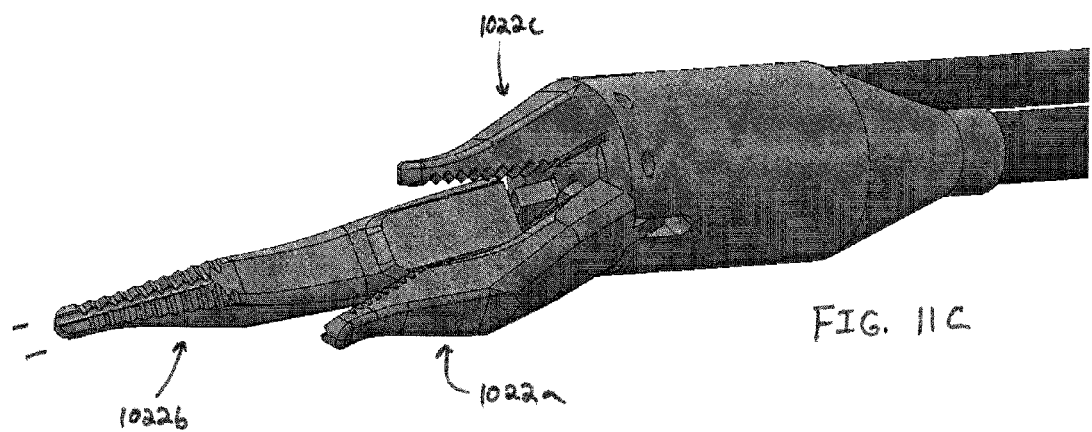
FIG. 11C is a perspective view of the end effector of FIG. 10, depicting one of the jaws of the end effector in a retracted position.

With reference now to FIGS. 11A-C, the end effector 1020 can be actuated such that the three jaws 1022a-c can be moved between various positions relative to one another. As shown in FIG. 11A, for example, the jaws 1022a-c can have an open configuration in which the distal ends 1026a-c of the three jaws 1022a-c are spaced apart from one another. Subsequent actuation of the primary trigger 1064 can be transmitted through the primary actuator 1042 such that the first and second jaws 1022a,b, which can be coupled to the primary actuator as discussed above, pivot to a closed position in which their longitudinal axis is aligned with the longitudinal axis of the end effector 1020, as shown in FIG. 11B. In such a position, the distal ends 1026a,b can contact one another, as well as the distal end 1026c of the third jaw 1022c when in its axially extended position. On the other hand, actuation of the secondary trigger 1066 when the jaws 1022a-c are in their position shown in FIG. 11A can be effective to move the third jaw 1022c proximally to its retracted position, as shown in FIG. 11C. As will be appreciated by a person skilled in the art, in some embodiments, the first and second jaws 1022a,b can be selectively biased to one of their open position or closed positions, while the third jaw 1022c can be selectively biased to its retracted or extended position.

The jaws 1022a-c can be coupled to the primary and secondary actuators 1042, 1044 in variety of manners that allow for the various movements of the jaws 1022a-c. By way of example, the jaws 1022a,b can be coupled to the distal end of the primary actuator 1042 through rivets such that longitudinal (i.e., axial) movement of the primary actuator 1042 is effective to move the first and second jaws 1022a,b between their open and closed positions, as discussed otherwise herein. Similarly, the third jaw 22c can be integral with or coupled to the distal end of the secondary actuator 1044 such that longitudinal movement of the secondary actuator 1042 is effective to move the third jaw 1022c between its retracted and extended positions. Moreover, the jaws 1022a-c can be disposed in variety of positions around the longitudinal axis (L) of the end effector 1020.

As will be appreciated by a person skilled in the art, though the jaws 1022a-c are depicted as being substantially identical, each of the jaws 1022a-c can differ and can have a variety of configurations that enables the end effector 1020 to grasp and/or dissect tissue. Referring now to FIG. 12, an exemplary first jaw 1022*a* is shown in further detail. The first jaw 1022*a* can have a variety of configurations but generally includes a proximal end 1027 having a proximal extension 1030 that is configured to movably couple to the primary actuator 1042 and a distal end 1026*a* that tapers to a point. As will be appreciated by a skilled in the art, the retractable third jaw 1026*c* can instead include a proximal end 1027 that is configured to engage the secondary actuator 1044 without necessarily enabling for the angular displacement of the third jaw 1022*c* relative to the longitudinal axis of the end effector 1020. By way of example, the third jaw 1022*c* can be integral with, or alternatively fixedly or removably coupled to, the distal end of the secondary actuator 1044 such that longitudinal movement of the secondary actuator 1042.

As shown in FIG. 11A and discussed otherwise herein, though the distal ends 1026*a-c* of the jaws 1022*a-c* are in direct contact with one another in the closed position, the jaws 1022*a-c* can be shaped so as to define an opening 1023 therebetween extending along the longitudinal axis of the end effector 1020. By way of example, with reference again to FIG. 12, the first jaw 1022*a* can include an intermediate portion 1033 between its distal and proximal ends 1026*a* that is spaced a distance from the longitudinal axis (L) when the jaws 1022*a-c* are in the closed position, unlike the distal ends 1026*a-c* which come together at the longitudinal axis.

As noted above, the shape of the distal ends 1026*a-c* of the jaws 1022*a-c* can also vary depending, for example, on the intended use of the device. Whereas the end effector 20 discussed above in reference to FIGS. 1-8 has a cylindrical shape of substantially constant diameter along its length which terminates in a blunt distal-most surface so as to minimize damage and/or avoid accidentally piercing tissue at the surgical site, the distal ends 1026*a-c* of the end effector 1020 have a pointed configuration so as to facilitate their insertion through tissue. As best shown in FIG. 11B, for example, the jaws 1022*a-c* can be shaped such that their proximal ends 1027 and intermediate portions 1033 together form a cylinder of substantially constant cross-section. However, in the closed position, the diameter of the end effector 1020 can decrease along its length (e.g., near the distal end) so as to taper radially to a point. Further, whereas the jaws 22*a-c* flare at their distal end so as to increase the surface area of the end effector that can be in contact with tissue, the width of each of the jaws 1022*a-c* tapers from its intermediate portion 1033 to its distal end 1026*a-c*. That is, the intermediate portion of the jaw 1022*b*, for example, has a width ($W_2$) that is greater than the width ($W_1$) of its distal end 1026*b*, as shown in FIG. 11A.

As discussed above, the inner radial surface of the distal tip 1026 can additionally include two substantially planar engagement surfaces 1029*a,b* that are configured to engage the corresponding planar engagement surfaces of the adjacent jaws when the end effector 1020 is in the closed position. The substantially planar engagement surfaces 1029*a,b* can additionally include surface features formed thereon to facilitate engagement between the jaws 1022*a-c* or engagement with tissue disposed between the jaws 1022*a-c*. In such a manner, the jaws 1022*a-c* can nest with one another in their closed positions, thereby resulting in an end effector having a substantially cylindrical intermediate portion which tapers to a distal tip. As will be appreciated by a person skilled in the art, the shape and size of the end effector 1020 in the closed position can vary depending on the configuration and relative positioning of the jaws 1022*a-c*, the shape and size of the access port and the surgical site, and its intended use.

The substantially planar engagement surfaces 1029*a,b* can have a variety of configurations, but generally are of a smaller area relative to the engagement surfaces 29*a,b* of the jaws 22*a-c* discussed above due to tapering of the distal end 1026*a-c*. As above, the two planar engagement surfaces 1029*a,b* can extend at a variety of angles relative to one another. For example, each engagement surface 1029*a,b* in the pair on each jaw 1022*a-c* extends at an obtuse angle (e.g., about 120°) relative to the other engagement surface in the pair on the same jaw. This angle can vary, however, depending on the positioning of the jaws 1022*a-c* relative to one another as otherwise discussed herein.

Figure 13A:
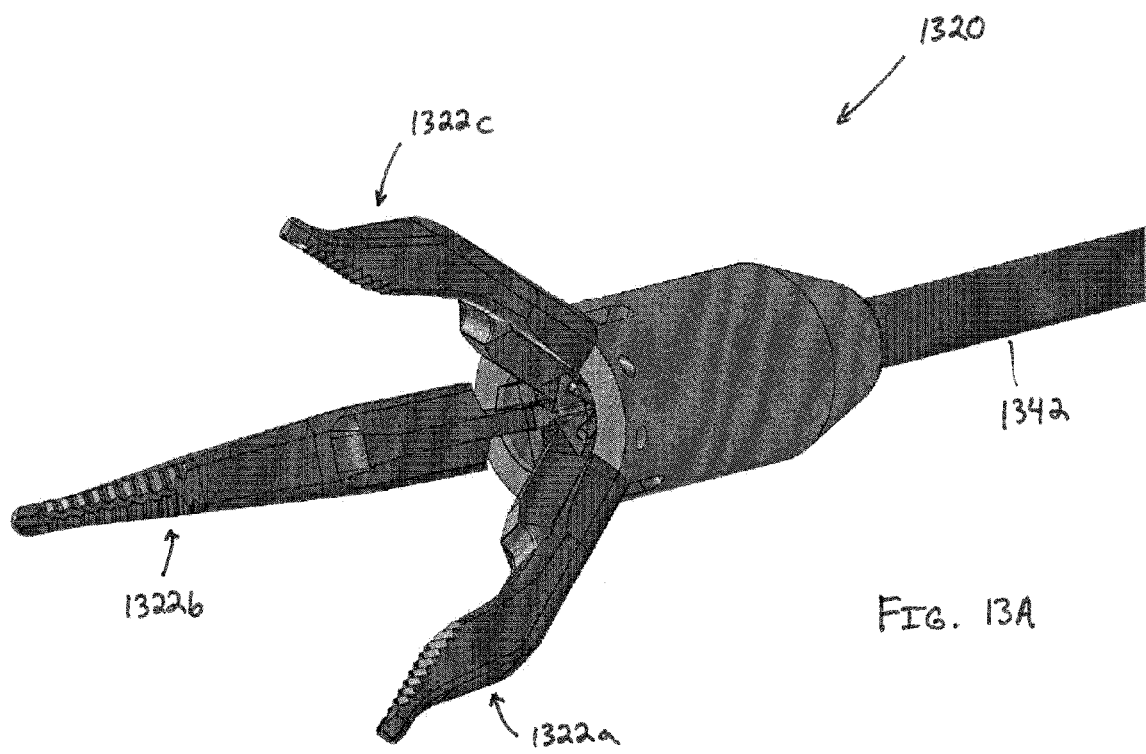
FIG. 13A is a perspective view of the distal end of another exemplary embodiment of a surgical device having an exemplary three-jawed end effector, depicting the end effector in an open configuration.
Figure 13B:
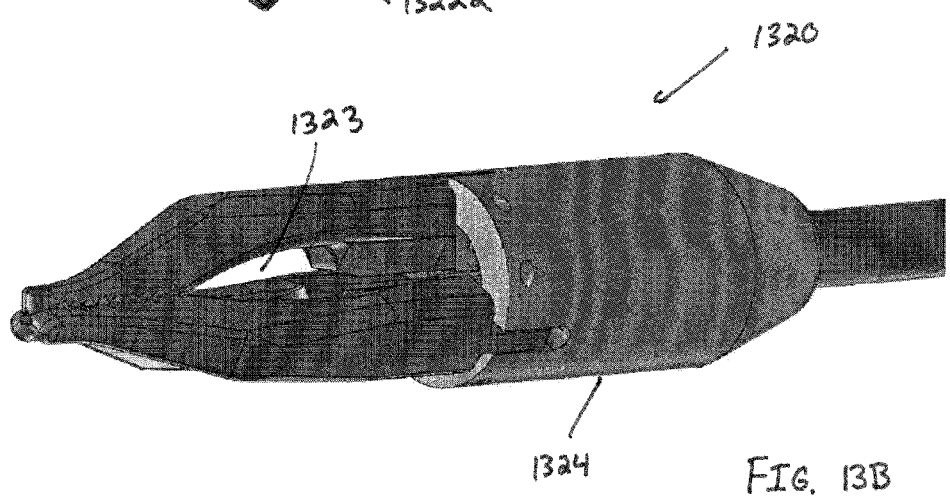
FIG. 13B is a perspective view of the distal end of the end effector of FIG. 9A, depicting the end effector in an open configuration.

With reference now to FIGS. 13A and 13B, another exemplary embodiment of an end effector 1320 according to the teachings herein is depicted. The end effector 1320 is substantially similar to that described above with reference to FIG. 9, for example, in that the end effector 1320 includes three jaws 1322*a-c*, each of which is movable between an open position in which the distal ends of the three jaws 1322*a-c* are spaced apart from one another, and a closed position in which the distal ends directly contact one another and define an opening 1323 therebetween. Likewise, a single actuator 1342 is effective to control the movement of the three jaws 1322*a-c*.

The end effector 1320 substantially differs from the end effector 920 in that the three jaws 1322*a-c* are particularly suited for dissecting tissue. As discussed above with reference to the jaws 1022*a-c*, the distal ends 1026*a-c* of the jaws are pointed to as to facilitate insertion through tissue. Unlike the jaws 1022*a-c* depicted in FIG. 10, however, the third jaw 1322*c* is configured to pivot between an open position and a closed position, as discussed otherwise herein.

Figure 10:
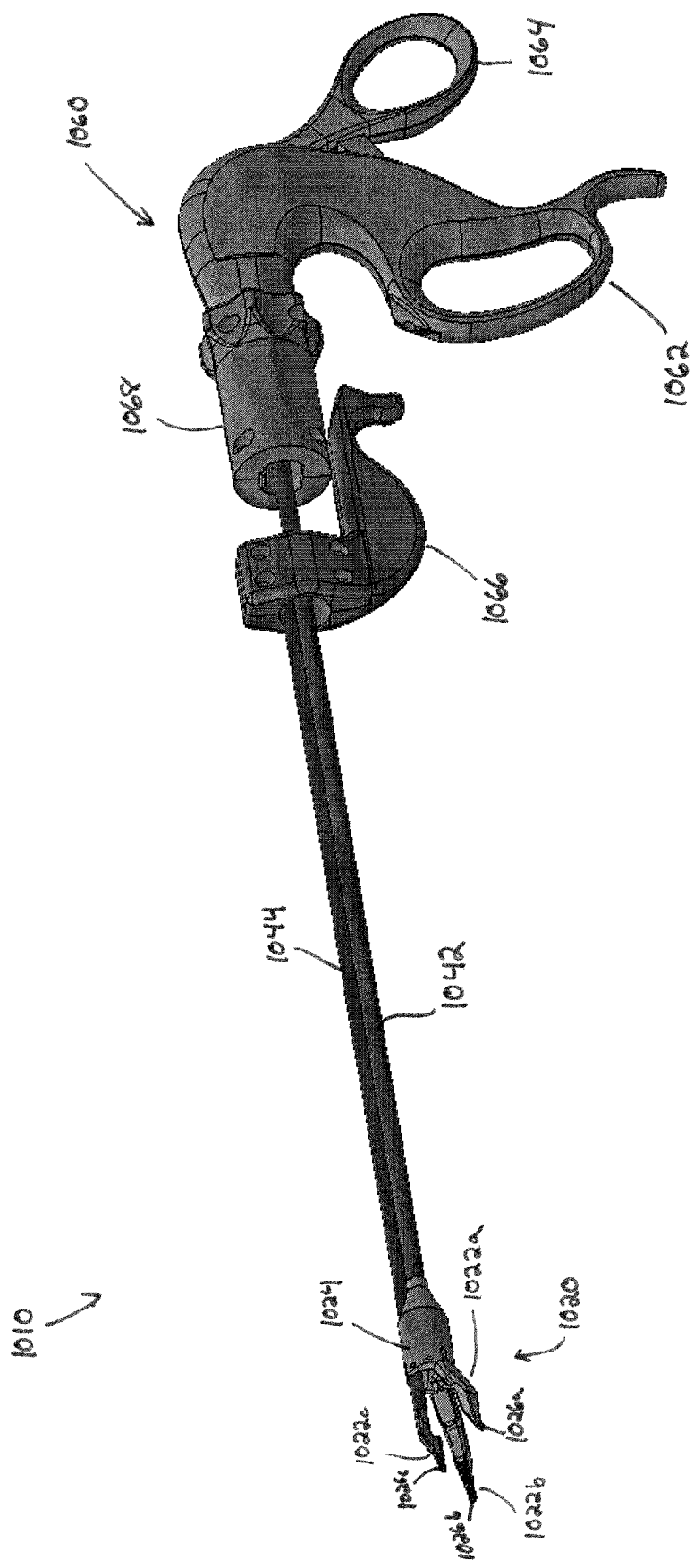
FIG. 10 is a perspective view of another exemplary embodiment of a surgical device having an exemplary three-jawed end effector.

The end effectors 1020, 1320 depicted in FIGS. 10 and 13, for example, can be used substantially as discussed above with reference to the end effector 20 depicted in FIGS. 1-8 (e.g., to grasp tissue), but additionally can better enable the user to dissect tissue. By way of example, the end effector 1020 can be delivered to the surgical site in the closed position as shown in FIG. 11B and can be further manipulated such that the distal ends 1126 of the three jaws 1122*a-c* pierce the tissue. After being inserted into the tissue in its closed position, the end effector 1120 can be actuated to move to its open position, as shown in FIG. 11A, thereby dissecting (e.g., separating the tissue). Whereas a tissue dissector having only two jaws is limited to generating a slit in tissue, the end effector 1020 can improve access by generating a more circular access "hole" in tissue through the separation of its three jaws 1022*a-c* in three different directions.

Further, the non-pivoting, axially-retractable independent jaw 1022*c* of the end effector 1020 depicted in FIG. 10 can advantageously provide additional functionality. By way of example, the end effector 1020 can be positioned at a surgical site within the body such that the outer edge of the retractable third jaw 1022*c* (e.g., along its longitudinal edge) contacts a tissue surface (e.g., a bone). The first and second jaws 1022*a,b* can be pivoted to dissect the tissue from the surface and subsequently returned to their closed position. The end effector 1020 can then be advanced along the surface, with the third jaw 1022*c* remaining in contact therewith, and the first and second jaws 1022*a,b* can again be actuated to their open position. In such a manner, the third jaw 1022*c* can act as a guide along the surface as the first and second jaws 1022*a,b* dissect tissue therefrom. Moreover, in some embodiments, the independent jaw 1022*c* can be actuated to an extended position beyond the distal end of the first and second jaws 1022*a,b* such that the third jaw 1022*c* alone can be effective to pierce tissue.

Similarly, the end effector 1020 can be particularly useful in circumstances in which movement of the jaws 1022*a-c* is desired in only two directions. By way of example, in an embodiment in which the first and second jaws 1022a,b are disposed about the longitudinal axis of the end effector 1020 such that they pivot in the same plane, as discussed otherwise herein, the end effector 1020 can be inserted through a bundle of nerves, for example, with the third jaw 1022c in its retracted position. As will be appreciated by a person skilled in the art, the end effector 1020 can be positioned within the nerve bundle such that subsequent actuation of the end effector 1020 can pivot the jaws 1022a,b in opposite directions along the length of the nerves, thereby preventing the nerves from being accidentally damaged.

In one embodiment, energy can be delivered through the end effectors 1020 and 1320 to cauterize tissue. By way of example, the jaws can act as an electrode or can include an electrode disposed on a tissue contacting surface such that the user can elect to deliver energy to seal (e.g., cauterize, cut) the bleeding site. For example, an electrode, operating in either a bipolar or monopolar mode, can deliver RF energy to the grasped tissue or tissue that is in direct contact with the electrode.

Figure 14A:
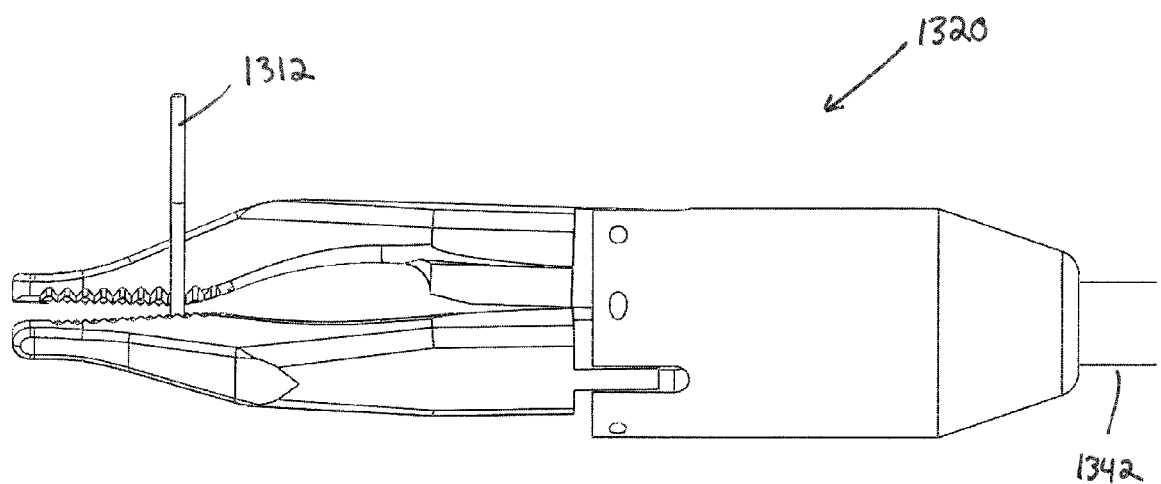
FIG. 14A is a side view of the end effector of FIG. 13A, depicting a needle being grasped thereby.
Figure 14B:
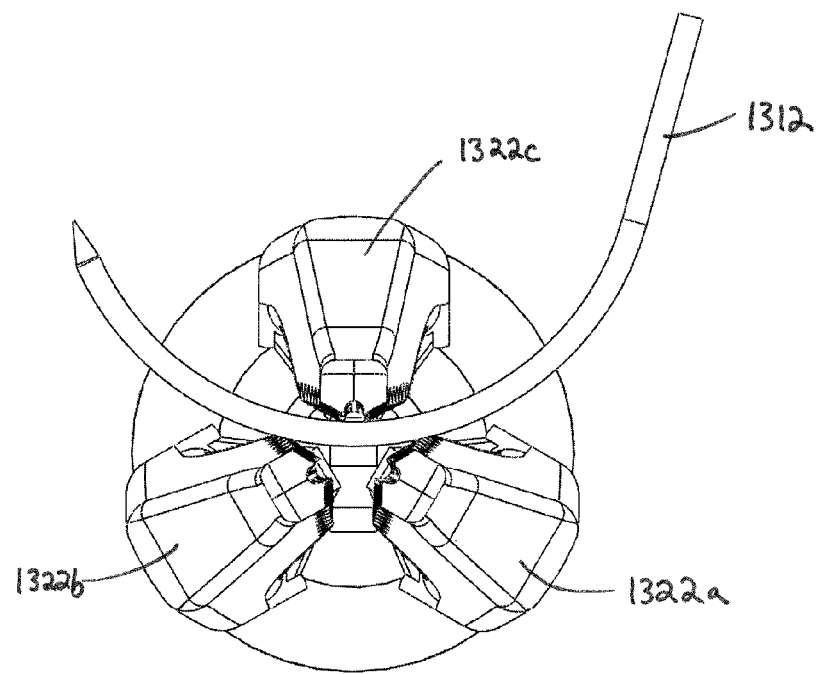
FIG. 14B is an end view of the end effector of FIG. 13A, depicting a needle being grasped thereby.

The end effectors disclosed herein can also be particularly useful in other surgical tasks such as, for example, holding a needle. As opposed to using two jaws to hold a needle for suturing tissue, the three jaws 1322a-c of the end effector 1320 can create three points of contact between the end effector 1320 and a needle. With reference now to FIGS. 14A and 14B, a curved needle 1312 for suturing tissue is depicted positioned within the jaws 1322a-c such that one of the jaws 1322c grasps the inside curvature of the needle 1312 while the other jaws 1322a,b engage the outside curvature. In this manner, a third jaw can provide an additional point of security in manipulating the needle 1312 relative to a two-jawed end effector. Moreover, the distal ends of the jaws 1322a-c can be configured to reliably engage the needle in a preferred position. For example, the jaws 1322a-c can be configured such that the needle 1312 rights itself within the jaws 1322a-c. In one embodiment, the needle 1312 can right itself within the jaws 1322a-c to an orientation such that the plane created by the needle 1312 is substantially perpendicular to the axis of shaft 1340.

A person skilled in the art will appreciate that any features of the various exemplary embodiments described herein can be used in conjunction with one another. By way of example, the retractable jaw 1022c, as depicted in FIG. 10, can be also used in conjunction with a end effector which is configured to pivot the third jaw 1022c. Similarly, the jaws 22a-c depicted in FIG. 1, for example, can be used with the device 1010 of FIG. 10. Further, energy can be applied by any of the end effectors described above to seal a puncture site and/or coagulate tissue. Moreover, a person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. By way of non-limiting example, the end effector can be removed, cleaned, sterilized, and reused. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
an end effector having first, second, and third non-cutting, atraumatic jaws movably coupled thereto, each jaw having a proximal end and a distal end, each jaw having a distal tip portion in the form of a substantially triangular prism having a first sidewall and a second adjacent sidewall, and each jaw being movable between an open position in which the distal ends of the three jaws are spaced apart from one another, and a closed position in which the first sidewall of each jaw is in direct contact with the second sidewall of an adjacent jaw.

2. The device of claim 1, wherein, when the jaws are in the closed position, the jaws have first, second, and third windows therebetween for accessing an opening formed between the jaws.

3. The device of claim 1, wherein the jaws are positioned symmetrically about a longitudinal axis of the end effector.

4. The device of claim 1, wherein at least one of the first, second, and third jaws is independently movable between the open position and the closed position relative to the other jaws.

5. The device of claim 1, wherein at least one of the jaws is configured to deliver energy to tissue.

6. The device of claim 1, wherein each first sidewall and each second sidewall extend at an obtuse angle relative to one another.

7. The device of claim 1, further comprising a handle, an elongate shaft extending distally from the handle, and an actuation mechanism extending through the elongate shaft between the handle and the end effector for moving the jaws between the open and closed positions.

8. The device of claim 1, wherein the end effector is rotatable relative to the handle.

9. The device of claim 1, wherein the first and second sidewalls each have a plurality of surface features formed thereon and spaced along a longitudinal length thereof.

10. The device of claim 9, wherein the plurality of surface features formed on adjacent jaws nest within one another when the jaws are in the closed position.

11. A surgical device, comprising:

an end effector having first, second, and third longitudinally extending jaws coupled thereto at a proximal end thereof and movable between open and closed positions, the first, second, and third jaws having non-cutting, atraumatic distal tips that directly contact one another in the closed position, each distal tip having first and second tissue contacting surfaces, and each tissue contacting surface having a plurality of surface features formed thereon and spaced along a longitudinal length thereof, and the first, second, and third jaws defining an opening therebetween in the closed position.

12. The device of claim 11, wherein, when the jaws are in the closed position, the jaws have first, second, and third windows therebetween for accessing the opening.

13. The device of claim 11, wherein the jaws are positioned symmetrically about a longitudinal axis of the end effector.

14. The device of claim 11, wherein the jaws define a substantially cylindrical cross-sectional shape taken along a longitudinal axis extending through the jaws when the jaws are in the closed position.

15. The device of claim 11, wherein at least one of the first, second, and third jaws is longitudinally retractable relative to the other jaws.

16. The device of claim 11, wherein each jaw has a distal tip with a substantially triangular shape.

17. The device of claim 11, wherein, when the jaws are in the closed position, each first tissue contacting surface directly contacts the first tissue contacting surface on the adjacent jaw, and each second tissue contacting surface directly contacts the second tissue contacting surface on the adjacent jaw.

18. The device of claim 11, wherein each first sidewall and each second sidewall extend at an obtuse angle relative to one another.

\* \* \* \* \*